(12) United States Patent
Walser et al.

(10) Patent No.: US 10,449,118 B2
(45) Date of Patent: *Oct. 22, 2019

(54) MANUFACTURE OF PEANUT FORMULATIONS FOR ORAL DESENSITIZATION

(71) Applicant: Aimmune Therapeutics, Inc., Brisbane, CA (US)

(72) Inventors: Bryan Walser, Menlo Park, CA (US); Howard V. Raff, Mill Valley, CA (US)

(73) Assignee: AIMMUNE THERAPEUTICS, INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/792,716

(22) Filed: Oct. 24, 2017

(65) Prior Publication Data
US 2018/0042816 A1    Feb. 15, 2018

Related U.S. Application Data

(63) Continuation of application No. 14/881,437, filed on Oct. 13, 2015, which is a continuation of application No. 14/207,165, filed on Mar. 12, 2014, now Pat. No. 9,198,869.

(60) Provisional application No. 61/784,964, filed on Mar. 14, 2013.

(51) Int. Cl.
| A61K 39/35 | (2006.01) |
| A61J 3/07 | (2006.01) |
| A61K 9/48 | (2006.01) |
| A61K 39/00 | (2006.01) |

(52) U.S. Cl.
CPC .............. *A61J 3/07* (2013.01); *A61K 9/4833* (2013.01); *A61K 9/4875* (2013.01); *A61K 39/35* (2013.01); *A61K 2039/542* (2013.01)

(58) Field of Classification Search
None
See application file for complete search history.

(56) References Cited

U.S. PATENT DOCUMENTS

| 3,809,767 A | 5/1974 | Sair et al. |
| 9,198,869 B2 | 12/2015 | Walser et al. |
| 9,492,535 B2 | 11/2016 | Walser et al. |
| 10,086,068 B2 | 10/2018 | Walser et al. |
| 2002/0018778 A1 | 2/2002 | Caplan |
| 2004/0234548 A1 | 11/2004 | Caplan |
| 2008/0317878 A1 | 12/2008 | Li et al. |
| 2012/0164306 A1 | 6/2012 | Girs |
| 2013/0090344 A1 | 4/2013 | Thakur et al. |
| 2014/0093541 A1 | 4/2014 | Clark et al. |
| 2014/0207105 A1 | 7/2014 | Laulicht et al. |
| 2014/0363470 A1 | 12/2014 | Koppelman et al. |
| 2016/0051593 A1 | 2/2016 | Raff et al. |
| 2017/0021012 A1 | 1/2017 | Walser et al. |
| 2019/0192652 A1 | 6/2019 | Walser |

FOREIGN PATENT DOCUMENTS

| JP | 2014-509606 A | 4/2014 |
| WO | WO-1992/15285 A1 | 9/1992 |
| WO | WO-2010/059534 A2 | 5/2010 |
| WO | WO-2010/059534 A3 | 5/2010 |
| WO | WO-2010/069595 A1 | 1/2012 |
| WO | WO-2012/123759 A1 | 9/2012 |
| WO | WO-2012/001074 A2 | 10/2012 |
| WO | WO-2013/087119 A1 | 6/2013 |
| WO | WO-2014/159609 A1 | 10/2014 |

OTHER PUBLICATIONS

Altschul, A.S. et al. (Sep. 2001). "Manufacturing and Labeling Issues for Commercial Products: Relevance to Food Allergy," *J. Allergy Clin. Immunol.* 108(3):468.
Anagnostou, K. et al. (Apr. 12, 2014, e-pub. Jan. 30, 2014). "Assessing the Efficacy of Oral Immunotherapy for the Desensitization of Peanut Allergy in Children (STOP II): A Phase 2 Randomized Controlled Trial," *The Lancet* 383(9925):1297-1304.
Bernard, H. et al. (2007, e-pub. Oct. 20, 2007). "Identification of a New Natural Ara h6 Isoform and of Its Proteolytic Product As Major Allergens in Peanut," *J. of Agricultural and Food Chem.* 55(23):9663-9669.
Blumchen, K. et al. (Jul. 2010). "Oral Peanut Immunotherapy in Children With Peanut Anaphylaxis," *J Allergy Clin Immunol.* 126(1):83-91.
Bock, S.A. et al. (Dec. 1988). "Doubleblind, Placebo-Controlled Food Challenge (DBPCFC) as an Office Procedure: A Manual,". *J Allergy Clin Immunol.* 82(6):986-997.
Bock, S.A. et al. (Oct. 1990). "Patterns of Food Hypersensitivity During Sixteen Years of Double-Blind, Placebo-Controlled Food Challenges," *J Pediatr.* 117(4):561-567.
Bock, S.A. et al. (Jan. 2001). "Fatalities Due to Anaphylactic Reactions to Foods," *J Allergy Clin. Immunol.* 107(1):191-193.
Bousquet, J. (2004). "Primary and Secondary Prevention of Allergy and Asthma by Allergen Therapeutic Vaccines," in *Allergens and Allergen Immunotherapy* 18:105-114.
Boyce, J.A. et al. (Dec. 2010). "Guidelines for the Diagnosis and Management of Food Allergy in the United States: Report of the NIAID-Sponsored Expert Panel," *J. Allergy and Clinical Immunology* 126(6):S1-S58.
Buchanan, A.D. et al. (Jan. 2007). "Egg Oral Immunotherapy in Nonanaphylactic Children With Egg Allergy," *J. Allergy Clin. Immunol.* 119:199-205.
Burks, W. et al. (1998). "Review Article Series II: Peanut Allergens," *Allergy* 53:725-730.
Burks, W. (2000). "Diagnosis of Allergic Reactions to Food," *Pediatr. Ann.* 29:744-752. [First page of Document Only].
Burks, W. (May 2002). "Current Understanding of Food Allergy," *Ann. NY. Acad. Sci.* 964:1-12.

(Continued)

*Primary Examiner* — Jessica Worsham
(74) *Attorney, Agent, or Firm* — Morrison & Foerster LLP

(57) ABSTRACT

The present application relates to a method for managing the development and manufacturing process of a therapeutically effective formulation. Peanut proteins are characterized from peanut flour and encapsulated formulations made using the peanut flour for oral immunotherapy of peanut allergies.

26 Claims, 9 Drawing Sheets

(56) References Cited

OTHER PUBLICATIONS

Burks, W. (Jun. 2003). "Skin Manifestations of Food Allergy," *Pediatrics* 111(6):1617-1624.
Burks, W. (Apr. 2003). "Peanut Allergy: A Growing Phenomenon," *J. Clin. Invest.* 111(7):950-952.
Burks, W. (2004). "Chapter 17:Food Allergens," *Clin. Allergy Immunol.* 18:319-337.
Burks, A.W. (2009). "Early Peanut Consumption: Postpone or Promote?," *J. Allergy Clin.Immunol.* 123(2):424-425.
Burks, A.W. et al. (Jul. 19, 2012). "Oral Immunotherapy for Treatment of Egg Allergy in Children," *N. Engl. J. Med.* 367:233-243.
Burks, W. (American Academy of Allergy, Asthma, and Immunology National Conference. Orlando, Florida, Mar. 6, 2012). 2012 American Academy of Allergy, Asthma & Immunology Annual Meeting. "Food Allergy" "Oral Immunotherapy for Food Allergens" "Food Allergy Guidelines" "Oral Desensitization in Patients with Food Allergy" Orlando, FL Mar. 2012, 108 pages.
Chen, X. et al. (2013, e-pub. Oct. 16, 2012). "Ara h2 and Ara h6 Have Similar Allergenic Activity and Are Substantially Redundant," *International Archives of Allergy and Immunology* 160:251-258.
Clark, A.T. et al. (2009). "Successful Oral Tolerance Induction in Severe Peanut Allergy," *Allergy* 64:1218-1220.
Fiocchi, A. et al. (Jul. 2006). "Food Allergy and the Introduction of Solid Foods to Infants: A Consensus Document," Ann. Allergy Asthma Immunol. 97:10-21.
Flinterman, A.E. et al. (2007). "Children With Peanut Allergy Recognized Predominantly Ara h2 and Ara h6, Which Remains Stable Over Time," *Clin. Exp. Allergy* 37:1221-1228.
Frew, A.J. (2003). "25. Immunotherapy of Allergic Disease," *J. Allergy Clin. Immunol.* 111(2 Suppl): S712-S719.
Fung, et al. (Jan. 8, 2013). "Relating Microarray Component Testing and Reported Food Allergy and Food-Triggered Atopic Dermatitis: A Real-World Analysis," Annals of *Allergy, Asthma & Immunology* 110(3):173-177.
Hofmann, A.M. et al. (Aug. 2009). "Safety of a Peanut Oral Immunotherapy Protocol in Children With Peanut Allergy," *J. Allergy Clin. Immunol.* 124:286-291, 14 pages.
Jones, S.M. et al. (Aug. 2009). "Clinical Efficacy and Immune Regulation With Peanut Oral Immunotherapy," *J. Allergy Clin. Immunol.* 124(2):292-30197, 20 pages.
Jones, S. M. et al. (2014). "State of the Art on Food Allergen Immunotherapy: Oral, Sublingual, and Epicutaneous," *J. Allergy Clin. Immunol.* 133:318-323.
Joshi, P.S. et al. (2002). "Interpretation of Commercial Food Ingredient Labels by Parents of Food-Allergic Children," *J. Allergy Clin. Immunol.* 109( 6):1019-1021.
Kapsenberg, M.L. et al. (Jun. 1999). "The Paradigm of Type 1 and Type 2 Antigen-Presenting Cells. Implications for Atopic Allergy," *Clin. Exp. Allergy* 29(Suppl 2):33-36.
Kim, E.H., et al. (Mar. 2011). "Sublingual Immunotherapy for Peanut Allergy: Clinical and Immunologic Evidence of Desensitization," *J. Allergy Clin. Immunol.* 127(3):640-646, 19 pages.
Koid, A. et al. (Jan. 8, 2014). "Ara h 6 Complements Ara h 2 as an Important Marker for IgE Reactivity to Peanut," *J. Agric. Food Chem.* 62(1):206-123, 18 pages.
Koid, A. et al. (2012). "Purified natural Ara h6: An Important Marker for IgE Response to Peanut," *J. Immunology* 188(1001):177. 15 Meeting Abstract Supplemental, 2 pages, (Abstract Only).
Koppelman et al. (Feb. 19, 1999). "Heat-Induced Conformational Changes of Ara h 1, A Major Peanut Allergen, Do Not Affect Its Allergenic Properties," *J. Biol. Chem.* 274(8):4770-4777.
Koppelman, S.J. et al. (2001). "Quantification of Major Peanut Allergens Ara h1 and Ara h2 in the Peanut Varieties Runner, Spanish, Virginia, and Valencia, Bred in Different Parts of the World," *Allergy* 56:132-137.
Koppelman, S.J. et al. (2004). "Relevance of Ara h1, Ara h2, and Ara h3 in Peanut Allergic Patients, As Determined by Immunoglobulin E Western Blotting, Basophil-Histamine Release, and Intracutaneous Testing: Ara h2 is the Most Important Peanut Allergen," *Clin. Exp. Allergy* 34:583-590.
Koppleman, S.J. et al. (2010). "Digestion of Peanut Allergens Ara h1, Ara h3 and Ara h6: A Comparative In Vitro Study and Partial Characterization of Digestion-Resistant Peptides," *Molecular Nutrition and Food Research* 54:1711-1721.
Krieg et al. (Apr. 6, 1995). "CpG Motifs in Bacterial DNA Trigger Direct B-Cell Activation," *Nature* 374:546-549.
Krimpenfort et al. (1988). "Transcription of T Cell Receptor β-Chain Genes is Controlled by a Downstream Regulatory Element," *EMBO J.* 7(3):745-750.
Kulis, et al. (Feb. 2012). The 2S Albumin Allergens of *Archis hypogaea*, Ara h 2 and Ara h 6, are the Major Elicitors of Anaphylaxis and Can Effectively Desensitize Peanut-Allergic Mice, *Clinical & Experimental Allergy: Journal of British Society for Allergy and Clinical Immunology* 42(2):326-336, 18 pages.
Lehmann, K. et al. (2006). "Structure and Stability of 2S Albumin-Type Peanut Allergens: Implications for the Severity of Peanut Allergic Reactions," *Biochem. J.* 395:463-472.
Lehrer, S.B. et al. (1999). "Immunotherapy for Food Allergies. Past, Present, Future," *Clin. Rev. Allergy Immunol.* 17(3):361-381.
Mondoulet et al. (Feb. 21, 2012). "Epicutaneous Immunotherapy (EPIT) Blocks the Allergic Esophago-Gastro-Enteropathy Induced by Sustained Oral Exposure to Peanuts in Sensitized Mice," *Plos One* 7(2):e31967, 10 pages.
Morishita M. et al. (Oct. 2006). "Is the Oral Route Possible for Peptide and Protein Drug Delivery?" *Drug Discovery Today* 11(19/20):905-910.
Muheem, A. et al. (2014). "A Review on the Strategies for Oral Delivery of Proteins and Peptides and Their Clinical Perspectives," *Saudi Pharmaceutical Journal*, 16 pages.
Narisety, S.D. et al. (Sep. 2009). "Open-Label Maintenance After Milk Oral Immunotherapy for IgE-Mediated Cow's Milk Allergy," *J. Allergy Clin. Immunol.* 124(3):610-612, 6 pages.
Nelson, H.S. et al. (1997). "Treatment of Anaphylactic Sensitivity to Peanuts by Immunotherapy With Injections of Aqueous Peanut Extract," *J. Allergy Clin. Immunol.* 99(6 Pt 1):744-751.
Oppenheimer, J.J. et al. (Aug. 1992). "Treatment of Peanut Allergy With Rush Immunotherapy," J. Allergy Clin. Immunol. 90(2):256-262.
Pele, M. (2010). "Peanut Allergens," *Romanian Biotechnological Letters* 15(2):5204-5212.
Pingali et al. (May 16, 2011, e-pub. Feb. 26, 2011). "Mixing Order of Glidant and Lubricant—Influence on Powder and Table Properties," *Int. J. Pharm.* 409:269-277, 22 pages.
Pisetsky, D.S. (Oct. 1996). "Immune Activation by Bacyterial DNA: A New Genetic Code," Immunity 5:303-310.
Poms, R.E. et al. (2004). "Effect of Roasting History and Buffer Composition on Peanut Protein Extraction Efficiency," *Mol. Nutr. Food Res.* 48:459-464.
Porterfield, H.S. et al. (Jul. 2009). "Effector Activity of Peanut Allergens: A Critical Role for Ara h2, Ara h6 and Their Variants," *Clin. Exp. Allergy* 39(7):1099-1108, 19 pages.
Sampson, H.A. et al. (2005). "Symposium on the Definition and Management of Anaphylaxis: Summary Report," *J. Allergy Clin. Immunol.* 115(3):584-591.
Schmitt, D.A. et al. (2010, e-pub. Dec. 22, 2009). "Processing Can Alter the Properties of Peanut Extract Preparations," *J. Agric. Food Chem.* 58:1138-1143.
Secrist, H. et al. (Mar. 1995). "Interleukin 4 Production by CD4+ T Cells From Allergic Individuals is Modulated by Antigen Concentration and Antigen-Presenting Cell Type," *J. Exp. Med.* 181(3):1081-1089.
Sen, M. et al. (2002). "Protein Structure Plays a Critical Role in Peanut Allergen Stability and May Determine Immunodominant IgE-Binding Epitopes," *The Journal of Immunology* 169:882-887.
Sicherer, S.H. et al. (Jul. 1998). "Clinical Features of Acute Allergic Reactions to Peanut and Tree Nuts in Children," *Pediatrics* 102(1):1-6.
Sicherer, S.H. (Nov. 1999). "Food Allergy: When and How to Perform Oral Food Challenges," *Pediatr. Allergy Immunol.* 10(4):226-234.

(56) References Cited

OTHER PUBLICATIONS

Sicherer, S.H. et al. (May 2010). "Immunologic features of Infants With Milk or Egg Allergy Enrolled in an Observational Study (Consortium of Food Allergy Research) of Food Allergy)," *J. Allergy Clin. Immunol.* 125:1077-1083, 14 pages.
Sicherer, S.H. et al. (Feb. 2014, e-pub. Dec. 31, 2013). "Food Allergy: Epidemiology, Pathogenesis, Diagnosis, and Treatment," *J. Allergy and Clinical Immunology* 133(2):291-307.
Singh, H. et al. (Oct. 2011). "Developing RP-HPLC Method for Detection of Peanut Allergens," in AACC International Annual Meeting, Oct. 16-19, 2011. Retrieved from the Internet <http://www.aaccnet.ora/meetings/Documents/2011Abstracts/p11ma199.htm> last visited Feb. 17, 2016, 1 page. (Abstract Only).
Skolnick, H.S. et al. (2001). "The Natural History of Peanut Allergy," *J. Allergy Clin. Immunol.* 107(2):367-374.
Skripak, J.M. et al. (Dec. 2008). "A Randomized, Double-Blind, Placebo-Controlled Study of Milk Oral Immunotherapy for Cow's Milk Allergy," *J. Allergy Clin. Immunol.* 122(6):1154-1160, 20 pages.
Skripak, J.M. et al. (2009). "Mammalian Milk Allergy: Avoidance Strategies and Oral Desensitization," *Curr. Opin. Allergy Clin. Immunol.* 9:259-264.
Thyagarajan, A. et al. (2009). "Basophil Suppression in Peanut Allergic Subjects undergoing Peanut Oral Immunotherapy (OIT)," *Journal of Allergy and Clinical Immunology* 123:S214-S214, Abstract No. 826, (Abstract Only).
Varshney, P. et al. (2011). A Randomized Controlled Study of Peanut Oral Immunotherapy: Clinical Desensitization and Modulation of the Allergic Response, *J. Allergy and Clinical Immunology* 127(3):654-660.
Vierk, K. et al. (2002). "Recalls of Foods Containing Undeclared Allergens Reported to the US Food and Drug Administration, Fiscal Year 1999," *J. Allergy Clin. Immunol.* 109(6):1022-1026.
Wang, J. et al. (Mar. 2011). "Food Allergy," *J. Clinical Investigations* 121(3):827-835.
Wilson, D.R. et al. (2005). "Sublingual Immunotherapy for Allergic Rhinitis: Systematic Review and Meta-Analysis," *Allergy* 60(1):4-12.
Yamamoto et al. (1992). "DNA From Bacteria, But Not From Vertebrates, Induces Interferons, Activates Natural Killer Cells and Inhibits Tumor Growth," *Microbial. Immunol.* 36:983-997.
Zhuang, Y. et al. (Sep. 5, 2012). "Redefining the Major Peanut Allergens," *Immunologic Research* 55(1-3):125-134.
Zimmerman et al. (1998). "Cutting Edge: CpG Oligodeoxynucleotides Trigger Protective and Curative Th1 Responses in Lethal Murine Leishmaniasis," *J. Immunol.* 160:3627-3630.
Australian Patent Examination Report No. 1, dated Mar. 31, 2013, for Australian Patent Application No. AU2014240404, 3 pages.
European Extended Search Report for European Application No. 14776121.7, dated Aug. 25, 2016, 8 pages.
European Communication Rule 114(2) for European Application No. 14776121.7, dated Oct. 12, 2017, 63 pages.
European Communication Rule 94(3) for European Application No. 14776121.7, dated Dec. 19, 2017, 9 pages.
European Communication Rule 70(2) and 70a(2) for European Application No. 1477621.7, dated Sep. 23, 2016, 1 page.
Response to Communication Rule 70a(2) for European Application No. 1477621.7, dated Mar. 26, 2017, 13 pages.
European Communication Rule 161(2) for European Application No. 1477621.7, dated Oct. 23, 2015, 2 page.
Response to Communication Rule 161(1) for European Application No. 1477621.7, dated Apr. 29, 2016, 12 pages.
International Preliminary Report on Patentability Search Report for PCT Application PCT/US2014/024401, dated Sep. 15, 2015, 10 pages.
International Search Report for PCT Application PCT/US2014/024401, dated Jul. 21, 2014, 6 pages.
International Search Report of PCT Application PCT/US2014/024405. dated Aug. 18, 2014, 5 pages.
Non-Final Office Action for U.S. Appl. No. 14/207,127, dated Nov. 6, 2015, 8 pages.
Non-Final Office Action for U.S. Appl. No. 15/276,440, dated Jan. 12, 2018, 13 pages.
Notice of Allowance for U.S. Appl. No. 14/207,127, dated Aug. 11, 2016, 8 pages.
Notice of Allowance for U.S. Appl. No. 14/207,165, dated Jul. 23, 2015, 10 pages.
Pre-interview First Office Action for U.S. Appl. No. 14/207,165, dated Mar. 12, 2015, 4 pages.
U.S. Appl. No. 15/870,477, Reyna et al, filed Jan. 12, 2018.(Copy not submitted herewith pursuant to waiver of 37 C.F.R. § 1.98(a)(2)(iii) issued by the Office on Sep. 21, 2004).
Fu, T.J. et al. (Jun. 19, 2013, e-pub. Apr. 8, 2013). "Impacted of Thermal Processing on ELISA Detection of Peanut Allergens," J. Agric. Food. Chem. 61(24):5649-5658.
Christensen, L.P. et al. (1995). "A Simple HPLC Method for the Isolation and Quantification of the Allergens Tuliposide A and Tulipalin A in *Alstroemeria,*" *Contact Dermatitis* 32:199-203.
European Oral Proceedings for European Application No. 1477621. 7, dated Mar. 27, 2019, 11 pages.
Non-Final Office Action for U.S. Appl. No. 16/289,370, dated Apr. 2, 2019, 7 pages.
Careri, M. et al. (2007, e-pub. Sep. 27, 2007). "Use of Specific Peptide Biomarkers for Quantitative Confirmation of Hidden Allergenic Peanut Proteins Ara h 2 and Ara h 3/4 for Food Control by Liquid Chromatography-Tandem Mass Spectrometry," *Anal. Bioanal. Chem.* 389(6):1901-1907.
Chassaigne, H. et al. (2007, e-pub. May 3, 2007). "Proteomics-Based Approach to Detect and Identify Major Allergens in Processed Peanuts by Capillary LC-Q-TOF (MS/MS)," *J. of Agricultural and Food Chemistry* 55:4461-4473.
Clinical Trial (Jul. 17, 2018). "Oral Desensitization to Peanut in Peanut-Allergic Children and Adults Using Characterized Peanut Allergen OT (ARC001)," NCT01987817.
Koppleman, S et al. (2012). "Abstract 1463—The Content of Allergens Arah1, Arah2, Ara h3, and Ara h6 in Different Peanut Cultivars Commonly Consumed in Europe and the USA," *Allergy* 67(Suppl. 96):458.
Podczek, F. et al. (1999). "The Filling of Granules Into Hard Gelatin Capsules," *International Journal of Pharmaceutics* 188(1):59-69.
Sampson, H. A. et al. (2011). "A Phase II, Randomized, Double Blind, Parallel Group, Placebo Controlled Oral Food Challenge Trial of Xolair (omalizumab) in Peanut Allergy," *J. Allergy Clin. Immunol.* 127(5):1309-1310.
Tan, S.B. et al. (1990). "Powder Flowability as an Indication of Capsule Filling Performance," *International Journal of Pharmaceutics* 61(1-2):145-156.
Summons to Attend Oral Proceeding Pursuant to Rule 115(1) EPC, mailed Oct. 25, 2018, for European Patent Application No. 14776121. 7, 7 pages.
Final Office Action for U.S. Appl. No. 14/881,437, dated Apr. 27, 2017, 16 pages.
Non-Final Office Action for U.S. Appl. No. 14/881,437, dated Jul. 28, 2016, 10 pages.
U.S. Appl. No. 16/111,102, Walser et al, filed Aug. 23, 2018. (Copy not submitted herewith pursuant to waiver of 37 C.F.R. § 1.98(a)(2)(iii) issued by the Office on Sep. 21, 2004).
U.S. Appl. No. 14/881,437, Walser et al, filed Oct. 26, 2015. (Copy not submitted herewith pursuant to waiver of 37 C.F.R. § 1.98(a)(2)(iii) issued by the Office on Sep. 21, 2004).
U.S. Appl. No. 14/835,336, Raff, filed Aug. 25, 2015. (Copy not submitted herewith pursuant to waiver of 37 C.F.R. § 1.98(a)(2)(iii) issued by the Office on Sep. 21, 2004).
U.S. Appl. No. 16/178,502, Dilly, filed Nov. 1, 2018. (Copy not submitted herewith pursuant to waiver of 37 C.F.R. § 1.98(a)(2)(iii) issued by the Office on Sep. 21, 2004).
Moutete et al. (1995). "Purification of Allergenic Proteins From Peanut for Preparation of the Reactive Solid Phase of a Specific IgE Radioimmunoassay," J. Chromatograph. B. 664:211-217.
Non-Final Office Action for U.S. Appl. No. 16/111,102, dated Jun. 27, 2019, 15 pages.

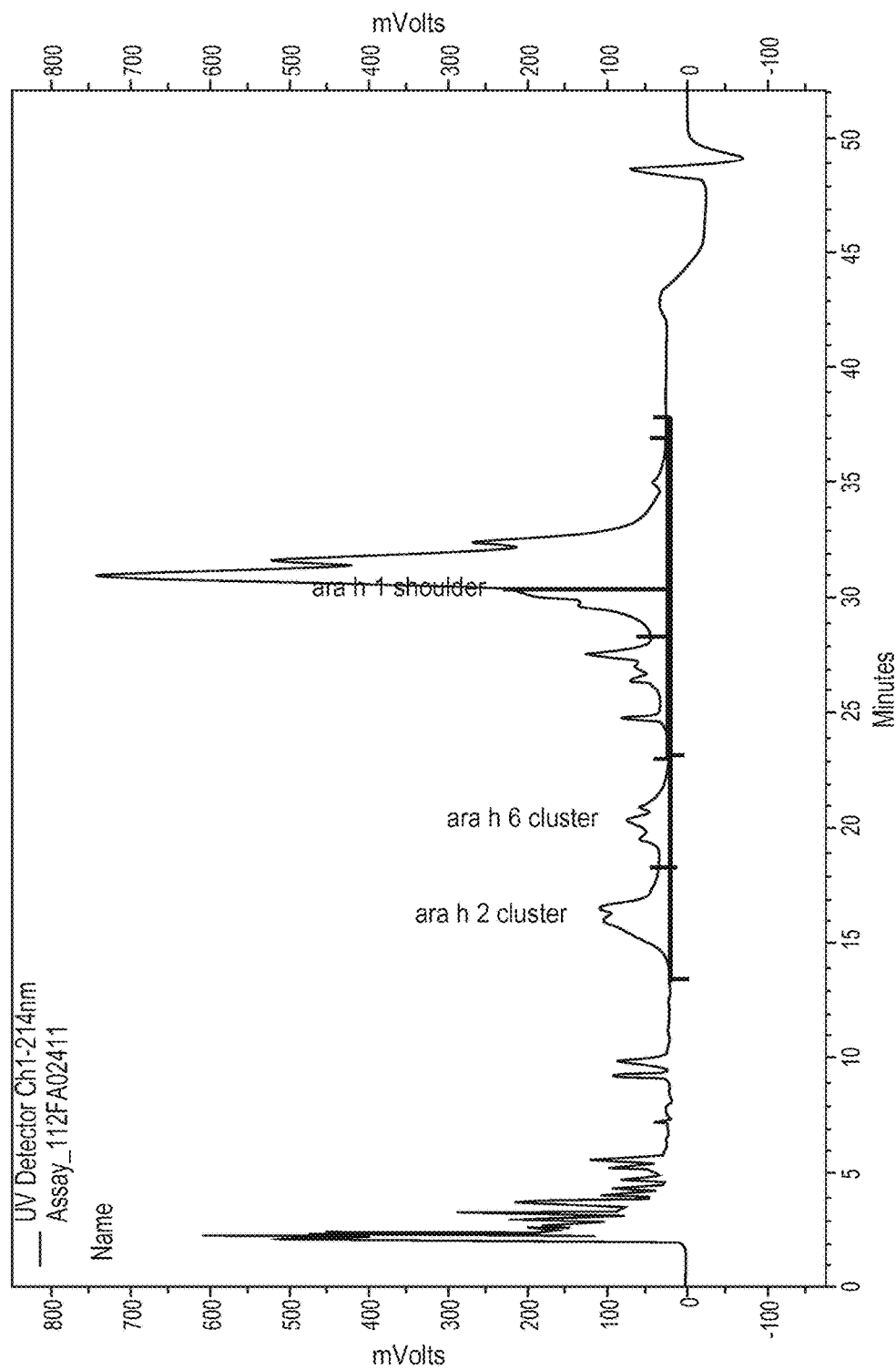

MANUFACTURE OF PEANUT FORMULATIONS FOR ORAL DESENSITIZATION

CROSS REFERENCE

This application is a continuation of U.S. patent application Ser. No. 14/881,437, filed on Oct. 13, 2015, entitled "MANUFACTURE OF PEANUT FORMULATIONS FOR ORAL DESENSITIZATION," now abandoned; which is a continuation of U.S. patent application Ser. No. 14/207,165, filed Mar. 12, 2014, entitled "MANUFACTURE OF PEANUT FORMULATIONS FOR ORAL DESENSITIZATION," now U.S. Pat No. 9,198,869, issued Dec. 1, 2015; which claims the benefit of U.S. Provisional Application No. 61/784,964, entitled "MANUFACTURE OF PEANUT FORMULATIONS FOR ORAL DESENSITIZATION," filed Mar. 14, 2013; each of which are incorporated herein by reference in their entirety.

This application is related to U.S. Provisional Application No. 61/784,863, filed Mar. 14, 2013, entitled "Peanut Formulations and Uses Thereof," which is incorporated herein by reference in their entirety.

BACKGROUND OF THE INVENTION

Allergies affect humans and companion animals and some allergic reactions (for example, those to insects, foods, latex, and drugs) can be so severe as to be life threatening.

Allergic reactions result when a subject's immune system responds to an allergen. Typically, there is no allergic reaction the first time a subject is exposed to a particular allergen. However, it is the initial response to an allergen that primes the system for subsequent allergic reactions. In particular, the allergen is taken up by antigen presenting cells (APCs; e.g., macrophages and dendritic cells) that degrade the allergen and then display allergen fragments to T-cells. T-cells, in particular CD4+"helper" T-cells, respond by secreting a collection of cytokines that have effects on other immune system cells. The profile of cytokines secreted by responding CD4+ T-cells determines whether subsequent exposures to the allergen will induce allergic reactions. Two classes of CD4+ T-cells (Th1 and Th2; T-lymphocyte helper type) influence the type of immune response that is mounted against an allergen.

The Th1-type immune response involves the stimulation of cellular immunity to allergens and infectious agents and is characterized by the secretion of IL-2, IL-6, IL-12, IFN-gamma, and TNF-beta by CD4+T helper cells and the production of IgG antibodies. Exposure of CD4+ T-cells to allergens can also activate the cells to develop into Th2 cells, which secrete IL-4, IL-5, IL-10, and IL-13. IL-4 production stimulates maturation of B cells that produce IgE antibodies specific for the allergen. These allergen-specific IgE antibodies attach mast cell and basophil receptors, where they initiate a rapid immune response to the next exposure to allergen. When the subject encounters the allergen a second time, the allergen is quickly bound by these surface-associated IgE molecules, resulting in the release of histamines and other substances that trigger allergic reactions. Subjects with high levels of IgE antibodies are known to be particularly prone to allergies.

SUMMARY OF THE INVENTION

Provided herein is a method of making a low dose capsule formulation useful in the methods provided here, comprising, (a) mixing peanut flour and diluent in a first blend; (b) adding about 45% of diluent in a second blend; (c) adding remaining diluent in a third blend; (d) adding a glidant and/or lubricant in a final blend; and (e) encapsulating blended powder in a capsule. In one embodiment, the diluent of step (a) comprises starch or lactose, microcrystalline cellulose (Avicel®), or dicalcium phosphate. In another embodiment, the diluent of step (b) and/or (c) comprises starch, lactose, microcrystalline cellulose (Avicel®), or dicalcium phosphate. In another embodiment, the glidant of step (d) glidant of step (d) comprises colloidal silicon dioxide (Cab-O-Sil), talc (e.g., Ultra Talc 4000), or combinations thereof. In another embodiment, the lubricant of step (d) comprises magnesium stearate. In one non-limiting example, the glidant comprises Cab-O-Sil. In one embodiment, step (d) comprises adding a glidant or a lubricant. In another embodiment, step (d) comprises adding a glidant and a lubricant. In another embodiment, the method further comprises sampling the blended mixture one or more times prior to encapsulation. In another embodiment, the dose comprises about 0.5 or about 1.0 mg peanut protein. In another embodiment of the described methods, step (d) further comprises passing the blended material through a mesh screen.

Provided herein is a method of making a higher dose capsule formulation useful in the methods provided here, comprising, (a) mixing peanut flour and diluent in a first blend; (b) discharging the blended material; (c) passing the blended material through a mesh screen and blending the screened material in a second blend; (d) adding in a glidant and/or lubricant in a third blend; and (e) encapsulating the blended powder. In one embodiment, the method optionally comprises sampling the blended material of step (d) one or more times prior to encapsulation. In yet another embodiment, the diluent of step (a) comprises starch, lactose or microcrystalline cellulose (Avicel®), or dicalcium phosphate. In another embodiment, the mesh screen of step (c) comprises a #20 mesh screen. In another embodiment, the glidant of step (d) glidant of step (d) comprises colloidal silicon dioxide (Cab-O-Sil), talc (e.g., Ultra Talc 4000), or combinations thereof. In another embodiment, the glidant of step (d) comprises Cab-O-Sil. In another embodiment, the lubricant of step (d) comprises magnesium stearate. In one embodiment, step (d) comprises adding a glidant or a lubricant. In another embodiment, step (d) comprises adding a glidant and a lubricant. In another embodiment, the dose comprises about 10, about 100 or about 475 mg peanut protein.

Provided herein is a method of making a capsule formulation useful in the methods provided here, comprising, passing peanut flour through a mesh screen; and encapsulating the blended powder. In one embodiment, the dose comprises about 475 mg peanut protein.

In any of such methods, the peanut flour may comprise characterized peanut proteins. In one embodiment, the peanut proteins comprise Ara h1, Ara h2 and Ara h6. The concentration of Ara h1, Ara h2 and Ara h6 may be characterized by RP-HPLC. In another embodiment, the concentration of Ara h1, Ara h2 and Ara h6 is at least an amount of a reference standard.

An encapsulated formulation produced by any of the methods described herein may be stable for at least about 3, 6, 9, 12, 18, 24, 36 or more months.

In one embodiment, the encapsulated formulation is stable at a temperature from about 2° C. to about 8° C. or from about 20° C. to about 30° C.

In another embodiment, the encapsulated formulation is stable at a temperature of about 20° C., about 21° C., about 22.5° C., about 23° C., about 24° C., about 25° C., about 26° C., about 27.5° C., about 28° C., about 29° C., or about 30° C.

A capsule size that may be used to hold the formulations produced by the methods described herein may be, for example, size 3, 00 or 000. In one embodiment, the capsule comprises Hydroxypropyl Methyl Cellulose (HPMC).

The methods described herein may further comprise storing a formulation in a container means. Any suitable container means may be used to store the encapsulated formulations described herein. In one embodiment, the container means may be, for example, a bottle. A bottle may be, for example, an amber-colored bottle in order to minimize exposure of the encapsulated formulations to ultraviolet light. In another embodiment, the container means further comprises a dessicant packet to control moisture content of the container means.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9: Chromatogram results from RP-HLPC analysis of 112FA02411 (GMP).

DETAILED DESCRIPTION OF THE INVENTION

Figure 1:
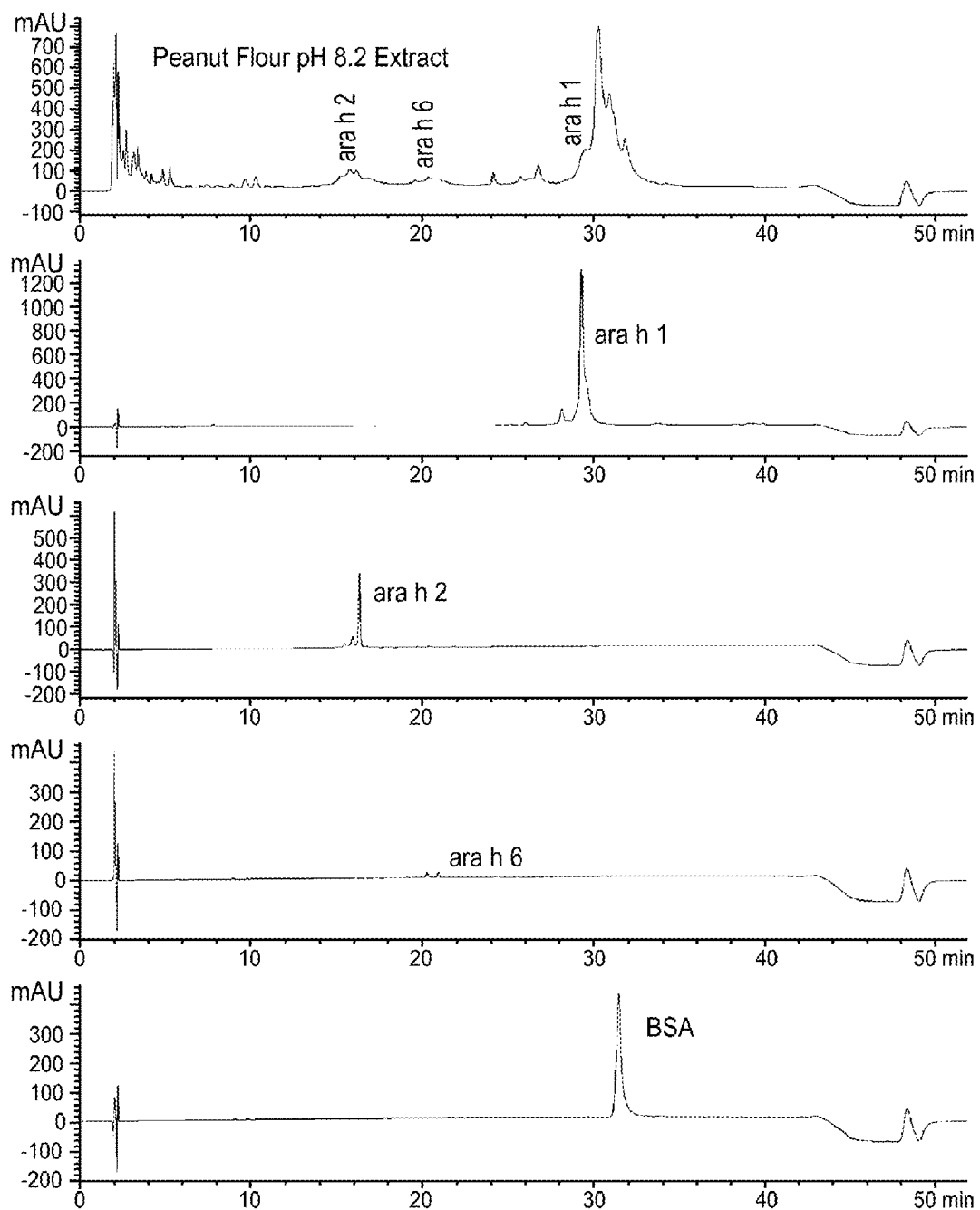
FIG. 1: Peanut flour extract at 214 nm using reversed phase HPLC. USDA Ara h standards, along with a 1 mg/mL BSA solution are also shown. The extracts are as follows: Top panel: Peanut flour, pH 8.2 extract; second panel: Ara h1 peak; third panel: Ara h2 peak; fourth panel: Ara h6 peak; bottom panel: 1 mg/ml BSA solution.

Disclosed herein are systems and methods that isolate proteins from peanut flour, which may be used to manufacture pharmaceutical compositions for treatment of peanut allergies. The systems and methods utilize high pressure (phase) liquid chromatography (HPLC) to capture Ara h1, Ara h2 and Ara h6 from peanut flour.

During the past decade, much has been learned about allergens in peanut. Peanuts are commonly associated with severe reactions, including life threatening anaphylaxis. The current standard of care in management of food allergy is dietary avoidance of the food and education of the subject/family in the acute management of an allergic reaction. The burden of avoidance and constant fear of accidental exposure negatively impacts the health-related quality of life for both subjects and their families. Quality of life surveys indicate that families with children having food allergies have significant impact on food preparation, social activities, finding appropriate childcare, school attendance, and level of stress among other things.

Currently, the only treatment for peanut allergy is a peanut-free diet and ready access to self-injectable epinephrine. However, strict avoidance diets can be complicated due to difficulty in interpreting labels and by the presence of undeclared or hidden allergens in commercially prepared foods. Accidental ingestions are unfortunately common, with up to 50% of food-allergic subjects having an allergic reaction over a two-year period. Allergic reactions to peanut can be severe and life threatening; and peanut and/or tree nut allergies account for the vast majority of fatal food-induced anaphylaxis. This combination of strict avoidance diets, the high incidence of accidental exposures, and the risk of severe or even fatal reactions with accidental exposures adds a tremendous burden and stress on subjects and their families. Further complicating matters is the fact that only about 20% of children will outgrow peanut allergy, meaning that the majority of people with peanut allergy will have it for the rest of their lives. If we couple the rising prevalence and increased consumption of peanut in Western countries with the facts that only approximately 1 in 5 will outgrow their allergy, that allergic reactions have the potential to be severe or even fatal, and that accidental exposures are common, developing an effective treatment for peanut allergy becomes even more imperative.

Specific immunotherapy for food allergy, in particular peanut allergy, in the forms of oral immunotherapy (OIT) and sublingual immunotherapy (SLIT) has been studied in recent years and has demonstrated encouraging safety and efficacy results in early clinical trials, including beneficial immunologic changes. OIT has shown evidence for inducing desensitization in most subjects with immunologic changes over time indicating progression toward clinical tolerance.

Peanut OIT: In Jones et al., peanut allergic children underwent an OIT protocol consisting of an initial dose escalation day, bi-weekly build-up (to 2 g) and daily maintenance phase followed by an OFC. After tolerating less than 50 mg peanut protein during an oral food challenge (OFC) at baseline, 27 of the 29 subjects ingested 3.9 g of peanut protein at the completion of OIT protocol.

Recently, Dr. Wesley Burks. (American Academy of Allergy, Asthma, and Immunology National Conference. Orlando, Fla., Mar. 6, 2012) presented work showing that 10 children with PA completed an OIT protocol and underwent an oral food challenge (OFC) 4 weeks after cessation of oral intake of peanut to evaluate the development of clinical "sustained unresponsiveness". Three out of 10 subjects passed the OFC; the authors considered these subjects as clinically tolerant. Over the course of treatment, peanut IgE levels lower than 85 kU/L at a time point of 3 months into OIT was predictive of subjects who became immune tolerant.

A multi-center double-blinded randomized placebo-controlled study reported by Varshney, et al., examined twenty-eight subjects. Three subjects withdrew early in the study because of allergic side effects. After completing up-dosing, a double-blind placebo-controlled food challenge was performed, in which all remaining peanut OIT subjects (n=16) ingested the maximum cumulative dose of 5000 mg (approximately 20 peanuts), whereas placebo subjects (n=9) could tolerate only a median cumulative dose of 280 mg (range, 0-1900 mg; p<0.001). In contrast with the placebo group, the peanut OIT group showed reductions in skin prick test size (P<0.001) and increases in peanut-specific IgG4 (P<0.001). Peanut OIT subjects had initial increases in peanut-specific IgE (P<0.01) but did not show significant change from baseline by the time of oral food challenge.

Definitions

Unless defined otherwise, all technical and scientific terms used herein have the same meaning as is commonly understood by one of skill in the art to which the inventions described herein belong. All patents and publications referred to herein are incorporated by reference.

The term "animal", as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

The term "antigen", as used herein, refers to a molecule that elicits production of an antibody response (i.e., a humoral response) and/or an antigen-specific reaction with T-cells (i.e., a cellular response) in an animal.

The term "allergen", as used herein, refers to a subset of antigens which elicit the production of IgE in addition to other isotypes of antibodies. The terms "allergen", "natural allergen", and "wild-type allergen" may be used interchangeably. Preferred allergens for the purpose of the present invention are protein allergens.

The phrase "allergic reaction", as used herein, relates to an immune response that is IgE mediated with clinical symptoms primarily involving the cutaneous (e.g., urticana, angiodema, pruritus), respiratory (e.g., wheezing, coughing, laryngeal edema, rhinorrhea, watery/itching eyes), gastrointestinal (e.g., vomiting, abdominal pain, diarrhea), and cardiovascular (i.e., if a systemic reaction occurs) systems. For the purposes of the present invention, an asthmatic reaction is considered to be a form of allergic reaction.

The phrase "anaphylactic allergen", as used herein, refers to a subset of allergens that are recognized to present a risk of anaphylactic reaction in allergic individuals when encountered in its natural state, under natural conditions. For example, for the purposes of the present invention, pollen allergens, mite allergens, allergens in animal danders or excretions (e.g., saliva, urine), and fungi allergens are not considered to be anaphylactic allergens. On the other hand, food allergens, insect allergens, and rubber allergens (e.g., from latex) are generally considered to be anaphylactic allergens. Food allergens are particularly preferred anaphylactic allergens for use in the practice of the present invention. In particular, legumes (peanuts), tree nut allergens (e.g., from walnut, almond, pecan, cashew, hazelnut, pistachio, pine nut, brazil nut), dairy allergens (e.g., from egg, milk), seed allergens (e.g., from sesame, poppy, mustard), soybean, wheat, and seafood allergens (e.g., from fish, shrimp, crab, lobster, clams, mussels, oysters, scallops, crayfish) are anaphylactic food allergens according to the present invention. Particularly interesting anaphylactic allergens are those to which reactions are commonly so severe as to create a risk of death.

The phrase "anaphylaxis" or "anaphylactic reaction", as used herein, refers to a subset of allergic reactions characterized by mast cell degranulation secondary to cross-linking of the high-affinity IgE receptor on mast cells and basophils induced by an anaphylactic allergen with subsequent mediator release and the production of severe systemic pathological responses in target organs, e.g., airway, skin digestive tract, and cardiovascular system. As is known in the art, the severity of an anaphylactic reaction may be monitored, for example, by assaying cutaneous reactions, puffiness around the eyes and mouth, vomiting, and/or diarrhea, followed by respiratory reactions such as wheezing and labored respiration. The most severe anaphylactic reactions can result in loss of consciousness and/or death.

The phrase "antigen presenting cell" or "APC", as used herein, refers to cells which process and present antigens to T-cells to elicit an antigen-specific response, e.g., macrophages and dendritic cells.

When two entities are "associated with" one another as described herein, they are linked by a direct or indirect covalent or non-covalent interaction. Preferably, the association is covalent. Desirable non-covalent interactions include, for example, hydrogen bonding, van der Walls interactions, hydrophobic interactions, magnetic interactions, etc.

The phrase "decreased anaphylactic reaction", as used herein, relates to a decrease in clinical symptoms following treatment of symptoms associated with exposure to an anaphylactic allergen, which can involve exposure via cutaneous, respiratory, gastrointestinal, and mucosal (e.g., ocular, nasal, and aural) surfaces or a subcutaneous injection (e.g., via a bee sting).

The term "epitope", as used herein, refers to a binding site including an amino acid motif of between approximately six and fifteen amino acids which can be bound by an immunoglobulin (e.g., IgE, IgG, etc.) or recognized by a T-cell receptor when presented by an APC in conjunction with the major histocompatibility complex (MHC). A linear epitope is one where the amino acids are recognized in the context of a simple linear sequence. A conformational epitope is one where the amino acids are recognized in the context of a particular three dimensional structure.

An allergen "fragment" according to the present invention is any part or portion of the allergen that is smaller than the intact natural allergen. In preferred embodiments of the invention, the allergen is a protein and the fragment is a peptide.

The phrase "immunodominant epitope", as used herein, refers to an epitope which is bound by antibody in a large percentage of the sensitized population or where the titer of the antibody is high, relative to the percentage or titer of antibody reaction to other epitopes present in the same antigen. In one embodiment, an immunodominant epitope is bound by antibody in more than 50% of the sensitive population, more preferably more than 60%, 70%, 80%, 90%, 95%, or 99%.

The phrase "immunostimulatory sequences" or "ISS", as used herein, relates to oligodeoxynucleotides of bacterial, viral, or invertebrate origin that are taken-up by APCs and activate them to express certain membrane receptors (e.g., B7-1 and B7-2) and secrete various cytokines (e.g., IL-1, IL-6, IL-12, TNF). These oligodeoxynucleotides contain unmethylated CpG motifs and when injected into animals in conjunction with an antigen, appear to skew the immune response towards a Th1-type response. See, for example, Yamamoto et al., *Microbiol. Immunol.* 36:983, 1992; Krieg et al., *Nature* 374:546, 1995; Pisetsky, *Immunity* 5:303, 1996; and Zimmerman et al., *J. Immunol.* 160:3627, 1998.

As used herein, the terms "comprising," "including," and "such as" are used in their open, non-limiting sense.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. In another embodiment, the use of the term "about" indicates that values slightly outside the cited values, i.e., plus or minus 0.1% to 5%, which are also effective and safe. In another embodiment, the use of the term "about" indicates that values slightly outside the cited values, i.e., plus or minus 0.1% to 2%, which are also effective and safe.

"Isolated" (used interchangeably with "substantially pure") when applied to polypeptides means a polypeptide or a portion thereof, which has been separated from other proteins with which it naturally occurs. Typically, the polypeptide is also substantially (i.e., from at least about 70% to about 99%) separated from substances such as antibodies or gel matrices (polyacrylamide) which are used to purify it.

Formulations

Formulations described herein include one or more active ingredients. Active ingredients may be isolated from peanut flour which may be obtained from any source such as, for example, the Golden Peanut Company. The peanut flour may be from about 10% to about 15%, or about 12% defatted peanut flour milled from lightly roasted peanuts. The peanut flour may be, in some instances, released by a supplier after standard analysis of content and microbiology, and may be stable for 9-12 months under refrigeration. The peanut flour may be formulated, encapsulated and tested prior to administration to a subject.

For analysis of the peanut flour, bulk substance (BS) and final formulation, a reverse phase HPLC assay (RP-HPLC) has been developed that separates three peanut flour protein allergens: Ara h1, Ara h2 and Ara h6. This assay forms the basis for identity and content testing at release and during stability. The reverse phase-HPLC assay may be utilized as an identification assay and to monitor lot-to-lot consistency and stability of the peanut allergens acceptable for production of the Characterized Peanut Allergen formulation.

Additional characterization of the protein allergens may also be performed using Enzyme Linked Immunosorbent Assays (ELISA) and gel analysis.

Peanuts and peanut flour are common foods and additives found in many food formulations. The intended clinical use for Characterized Peanut Allergen identified by the present inventors is found in relatively small quantities (0.5 to 4000 mg/dose) compared to quantities contained in food and may be delivered via the same route as orally ingested peanut-containing products.

Formulations described herein may be tested in a multi-center, placebo-controlled study to demonstrate the safety and efficacy of Characterized Peanut Allergen in subjects from about 4 to about 26 years of age with moderate-to-severe clinical reactions to peanut ingestion. Subjects with significant concomitant health conditions, uncontrolled asthma, or prior admission to an intensive care unit due to anaphylaxis may be excluded. Standard anti-allergy medications (e.g., antihistamines, oral corticosteroids, etc.) may be allowed on maintenance and while up-dosing with Characterized Peanut Allergen (CPA).

A formulation comprising Characterized Peanut Allergen (CPNA), may include peanut protein (comprising peanut allergen proteins Ara h1, Ara h2 and Ara h6) formulated with a one or more diluents, one or more glidants, one or more lubricants and, optionally, one or more filling agents, in graduated doses, comprising capsules containing about 0.5 mg, about 1 mg, about 10 mg, about 100 mg and about 1000 mg each of peanut protein. Each capsule may be opened and the content mixed into taste-masking food immediately prior to administration.

An active pharmaceutical ingredient is initially sourced as raw peanuts, *Arachis hypogaea*, a member of the legume family. Raw peanuts may be procured from multiple farming sources, where the shelled, raw peanuts are processed into 12% defatted roasted peanut flour (PF). The PF may be comprise a certificate of analysis (CofA) for further processing under cGMP conditions.

Formulation, fill and testing of the CPNA capsules may be performed at a cGMP contract manufacturing site. Under cGMP manufacturing conditions, the protein flour (PF), which is comprised of approximately 50% peanut protein w/w, is mixed with one or more diluents, one or more glidants and one or more lubricants.

In one embodiment, a composition comprises one or more diluents. "Diluents" for use in the formulations include, but are not limited to, alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), microcrystalline cellulose (e.g., Avicel®); silicified microcrystalline cellulse; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), lactose (e.g., lactose monohydrate, lactose anhydrous, etc.); dicalcium phosphate; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, a starch, e.g., a natural starch such as corn starch or potato starch, a pregelatinized starch such as Colorcon (Starch 1500), National 1551 or Amijel®, or sodium starch glycolate such as Promogel® or Explotab®; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and combinations thereof. In one embodiment, the formulation comprises microcrystalline cellulose or starch 1500. In another embodiment, the formulation comprises microcrystalline cellulose and starch 1500.

Suitable glidants (anti-caking agents) for use in the solid dosage forms described herein include, but are not limited to, colloidal silicon dioxide (Cab-O-Sil), talc (e.g., Ultra Talc 4000), and combinations thereof. In one embodiment, the composition comprises Cab-O-Sil.

Suitable lubricants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and combinations thereof. In one embodiment, the composition comprises magnesium stearate. In another embodiment, the composition comprises sodium stearyl fumerate.

In some embodiments, a formulation may further comprise one or more filling agents. "Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and combinations thereof.

Figure 7:
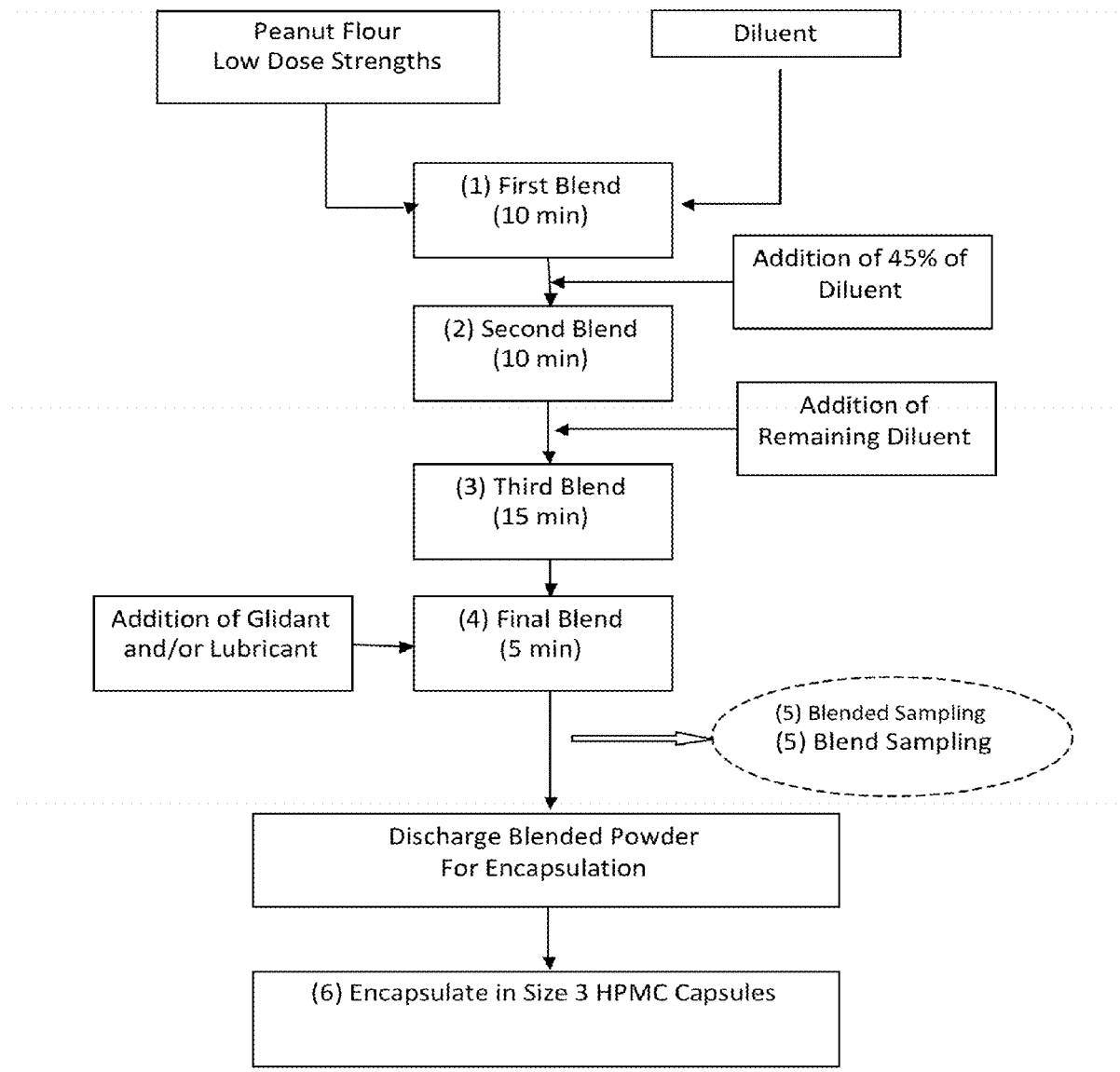
FIG. 7: Blending Process Flow Diagram for Low Dose Capsules (0.5 mg and 1 mg).
Figure 8:
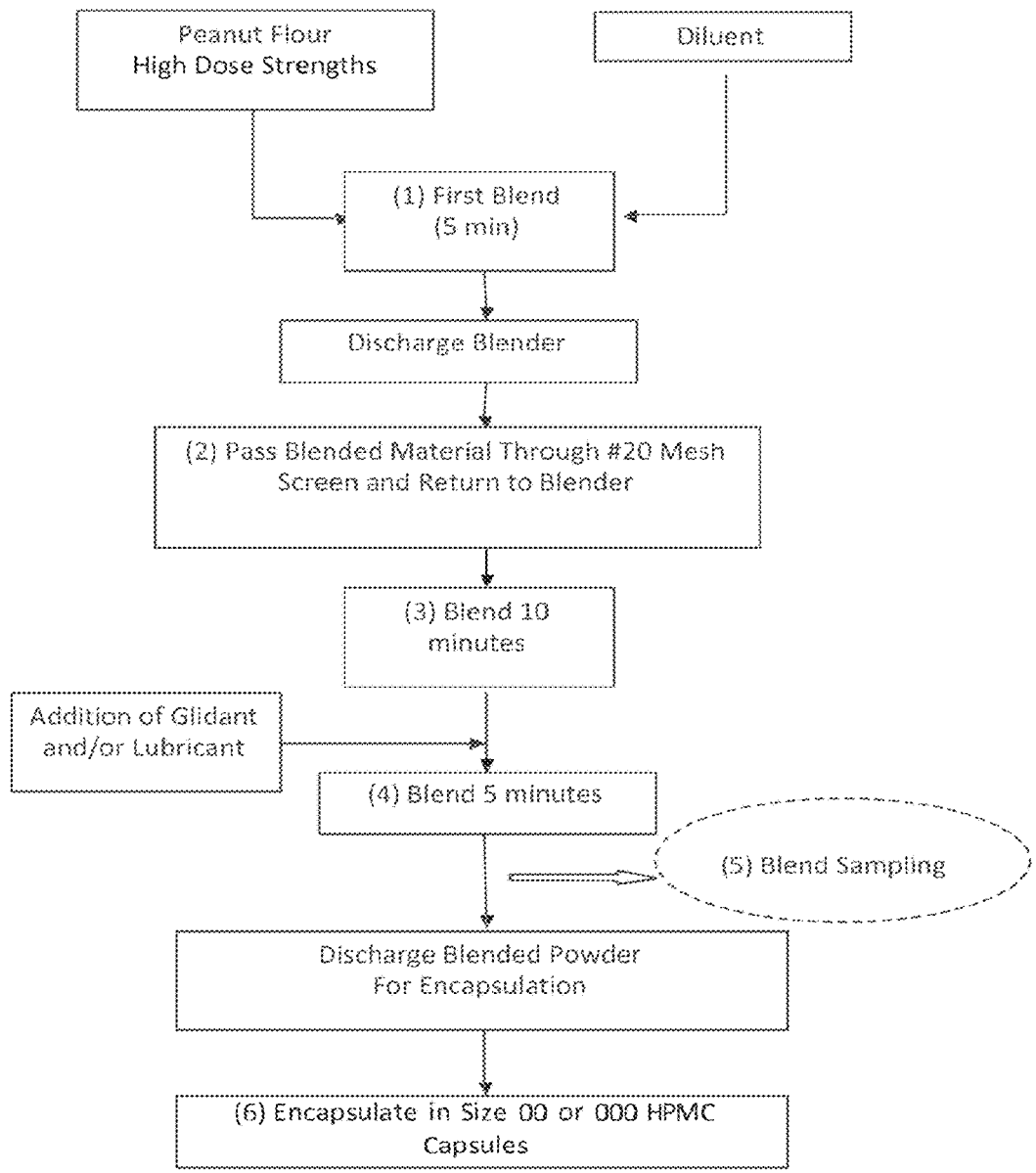
FIG. 8: Blending Process for the High Dose Capsules (at least 10 mg).

Ingredients described herein may be mixed according to, for example, the processes illustrated in FIGS. 7 and 8. Mixed formulations may be subsequently encapsulated as 0.5, 1, 10, 100 mg, 475 mg, and 1000 mg of peanut protein in size 3, 00 or 000. Hydroxypropyl Methyl Cellulose (HPMC) capsules. Compatibility studies may evaluate combinations of the peanut flour with one or more of the excipients, which may have in some instances, GRAS recognition. The diluent provides the opportunity to formulate the low and high doses to contain adequate volume for dispersal from the opened capsule. The glidant and lubricant add flowability to the PF such that the capsule is easily emptied of flour by the subject or practitioner at time of administration. For clinical trials, the capsules may be bulk packed into a container means such as, for example, bottles. In some instances, the container means may be treated to prevent (partially or fully) exposure to light. For example, a container means may be amber-colored. A container means may also, in some instances, contain a dessicant to prevent (partially or fully) exposure to moisture during shipping and storage. At the time of use, capsule(s) containing CPNA may be opened and the content mixed into taste-masking food immediately prior to administration.

In order to standardize the delivery of peanut protein allergens, a cGMP manufactured Characterized Peanut Allergen (CPNA) formulation has been developed. The protein content of the formulation is critical from two aspects. First, the total protein delivered should be consistent among batches, and second, the proportion of critical individual allergens should be controlled.

Total protein content of the bulk substance and final formulation release may be quantified using protein determination methods described herein which address current issues in the industry: namely, prior to the present application establishing the absolute or relative amounts of individual peanut protein allergens in the peanut flour is more problematic and has not been controlled.

Peanut protein is comprised of several individual protein allergens typically detectable by polyacrylamide gel electrophoresis and immunoblotting using allergen specific polyclonal antisera from allergic humans or immunized animals. Of these proteins, based on immunoblot, reactivity against crude peanut extracts by human sera from peanut allergic humans, and in vitro histamine release from sensitized basophils, Ara h1, Ara h2 and Ara h6 have been identified as allergenic peanut protein allergens, with Ara h2 and Ara h6 contributing the majority of the allergenic activity of crude peanut extract.

Prior to the present application peanut allergen proteins have typically been fractionated from crude peanut extracts by size exclusion chromatography (SEC) or polyacrylamide gel electrophoresis. These techniques may present a relative view into the spectrum of Ara proteins, but do not provide the resolution and sensitivity needed to compare individual peanut allergen expression among peanut flour lots, nor possible changes in protein structure over time. In order to address these limitations, the present inventors have developed a reverse phase HPLC (RP-HPLC) method to enhance the resolution and allow physical separation of peanut allergens Ara h1, Ara h2 and Ara h6.

An assay was developed for the determination and characterization of Ara h1, 2 and 6 allergenic proteins in roasted peanut flour. A simple single stage extraction procedure was modified using Tris buffer at pH 8.2, followed by centrifugation and filtration. Samples are prepared at 100 mg/mL and extracted at 60° C. for 3 hours. The final neat filtrate is suitable for direct analysis by HPLC.

The HPLC separation utilizes a reversed phase separation using a wide pore 300 Å silica column with a bonded butyl stationary phase. A binary gradient may be employed based upon 0.1% trifluoroacetic acid and acetonitrile. The mobile phase may be compatible with mass spectrometry. Detection may be accomplished with a UV detector at 214 nm, as sensitivity may be reduced with detection at 280 nm.

Specificity of the method may be determined by comparing the retention times and peak patterns of the whole peanut extract with Ara h proteins. The principle Ara h protein peaks, in some instances, may not resolve as discrete entities, but rather may appear as ensembles of many similar proteins. Thus, the Ara h1, Ara h2 and Ara h6 allergens may appear as clusters of peaks within a retention time region. Accordingly, the relative amount of a particular Ara h protein is then determined as the percentage of the total area within a defined elution region. Chromatographic resolution of the various regions is assessed, and the method may be useful for comparison of subtle differences in these regional patterns for different lots and sources of peanut flour proteins, and stability of the formulation.

A representative example chromatographic series at 214 nm is shown in FIG. 1 comparing the crude extract (top panel) with profiles from purified Ara h1, Ara h2 and Ara h6 proteins and BSA.

RP-HPLC method pre-qualification may be assessed by comparing three independent preparations of a single peanut flour lot, by comparing the results of replicate assays performed by two different analysts on two different days, or by comparing the results of independent preparations of different lots of peanut flour on the same or different days.

Precision may be estimated by performing the extraction of a single sample in triplicate, and analyzing the results according to the proposed method (see, e.g., Table 1). Triplicate extractions and determinations of a single lot of peanut flour are conducted; reported values are percent area of each Ara h species. Integration of the peaks may be performed by using forced integration events on a data system (e.g., ChemStation), or manual integration. The precision for these triplicate independent preparations of a single lot of peanut flour may range from about 1.1% relative standard deviation (RSD) for Ara h6 to about 18.3% for Ara h1. The higher (% RSD) for Ara h1 may be associated with integrating the Ara h1 shoulder from the subsequent larger cluster.

TABLE 1

RP-HPLC Method Precision

| Peanut Flour Lot # | % Area | | |
|---|---|---|---|
| | Ara h2 | Ara h6 | Ara h1 (shoulder) |
| 112FA02411 | 12.20 | 6.36 | 7.41 |
| | 11.95 | 6.30 | 9.68 |
| | 12.30 | 6.22 | 10.72 |
| Average | 12.15 | 6.30 | 9.27 |
| Std Dev | 0.1762 | 0.0718 | 1.6955 |
| % RSD | 1.45% | 1.14% | 18.29% |

A second precision method compares the results obtained by two different analysts performing the assay on two different days. Each value presented represents the average of duplicate injections. Table 2 provides exemplary results of a comparison of the percent area values and extractable protein content of three peanut flour lots, by two different analysts on different days. Comparison of the quantitative results obtained from these assays yields Ara h values that agree between 86% to 107%; total protein content may agree within 95%-102%. The percent of the match between the two analysts may also be presented.

TABLE 2

RP-HPLC Method Precision

| | % Area | | | | | |
|---|---|---|---|---|---|---|
| | Ara h2 | | Ara h6 | | Ara h1 (shoulder) | |
| Peanut Flour Lot # | Analyst 1 | Analyst 2 | Analyst 1 | Analyst 2 | Analyst 1 | Analyst 2 |
| 111FA36111 | 10.60 | 12.29 | 5.59 | 5.77 | 8.82 | 9.73 |
| % Match | 86.31 | | 96.76 | | 90.70 | |
| 111FA36211 | 10.65 | 12.02 | 5.48 | 5.67 | 11.14 | 9.36 |
| % Match | 88.58 | | 96.63 | | 118.97 | |
| 112FA02411 | 10.62 | 12.15 | 5.93 | 6.30 | 9.91 | 9.27 |
| % Match | 87.40 | | 94.12 | | 106.92 | |

Values are the average of two injections

Analysis of various PF lots may be used to demonstrate that the expression of Ara h1, Ara h2 and Ara h6 is consistent, both individually and relative to each other across lots of peanut flour. This assay may also form the basis for identity and content testing at release and during stability determination.

Figure 2:
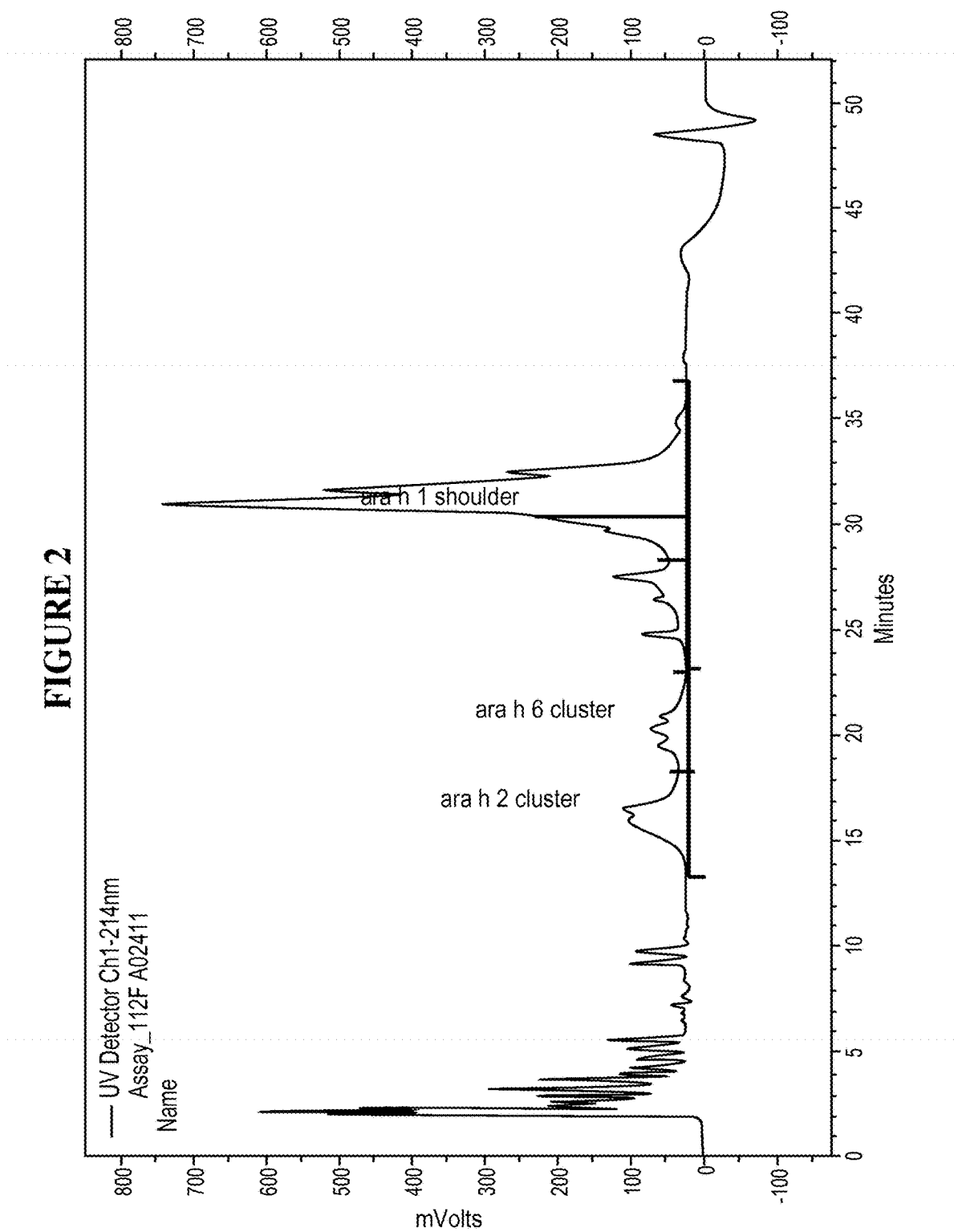
FIG. 2: Chromatograph results from RP-HPLC analysis of 112FA02411 (GMP).
Figure 3:
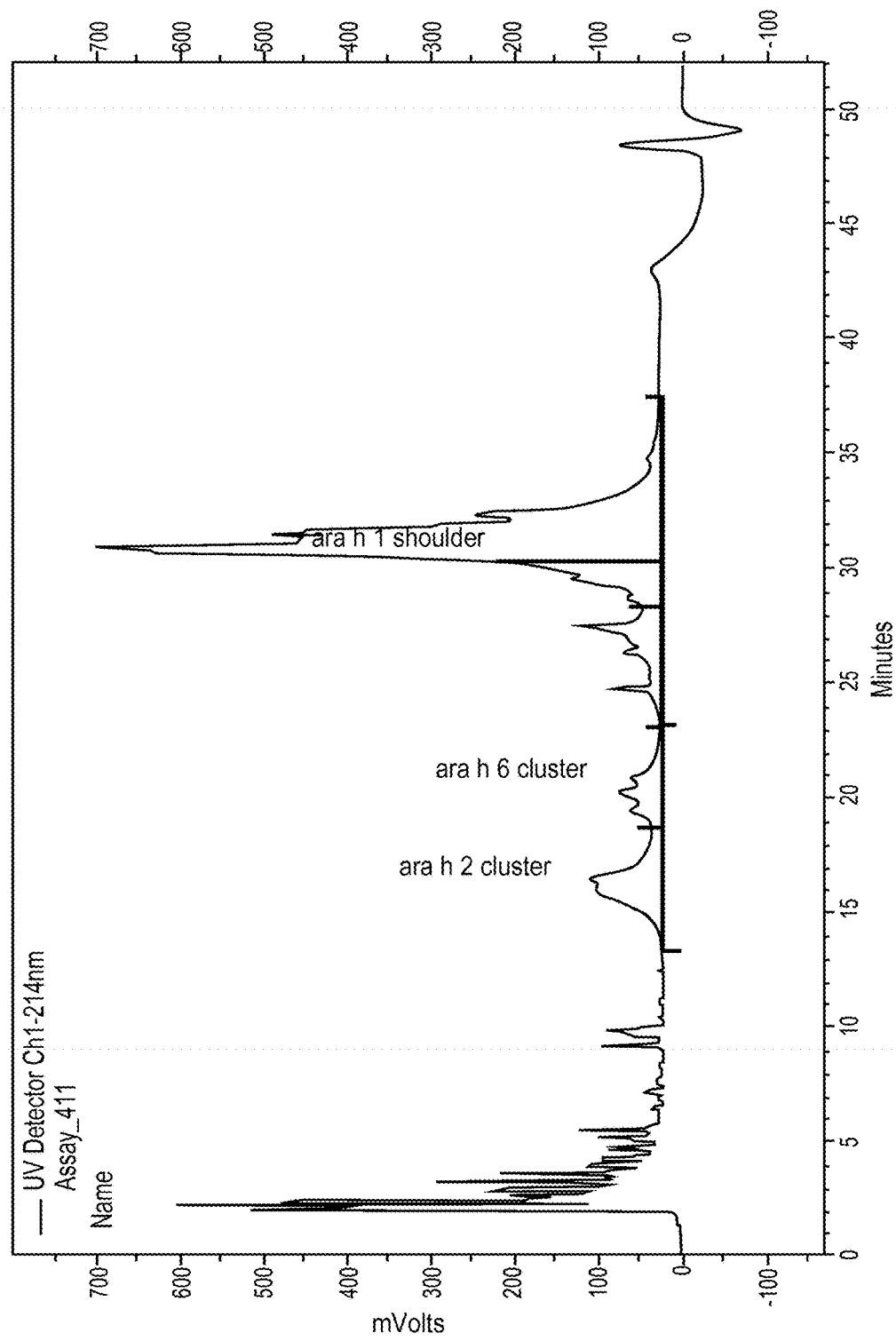
FIG. 3: Chromatograph results from RP-HPLC analysis of 112FA02411 (Non GMP).
Figure 4:
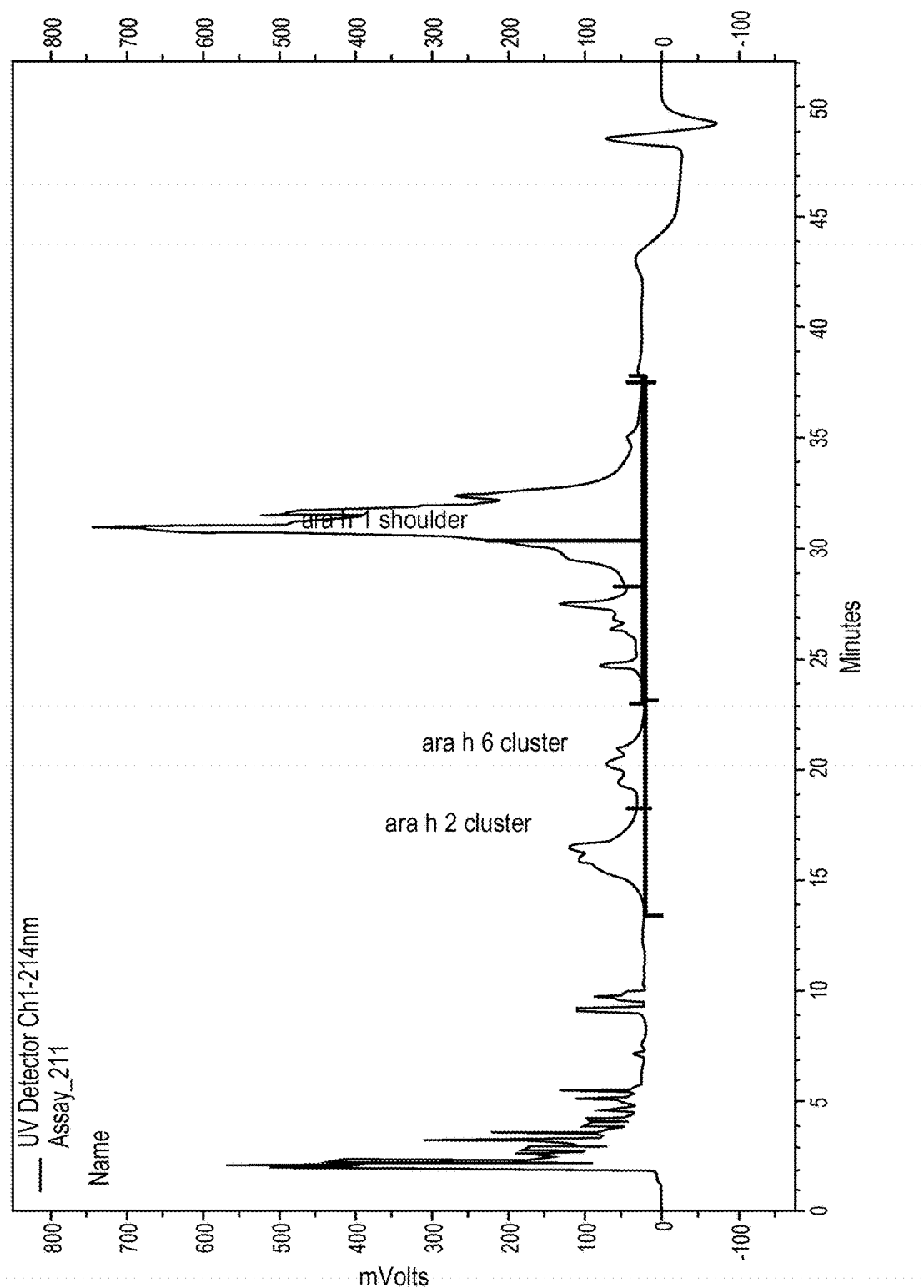
FIG. 4: Chromatograph results from RP-HPLC analysis of 111FA36211 (Non GMP).

The assay was be conducted and analyzed by a second cGMP manufacturer. The HPLC profiles (see, e.g., FIG. 2, FIG. 3 and FIG. 4), total protein and percentage of each allergen within the total protein (see, e.g., Table 3) are generally consistent between the assays performed by both laboratories using the same peanut flour lots (allows bridging of the data).

TABLE 3

Comparison for Ara h Proteins and Total Extractable Protein Content

| | % Area | | | |
|---|---|---|---|---|
| Peanut Flour Lot | Ara h2 (shoulder) | Ara h6 (shoulder) | Ara h1 (shoulder) | % Protein |
| 111FA36111 | 11.40 | 5.29 | 9.79 | 11.26 |
| 111FA36211 | 11.20 | 5.67 | 9.85 | 11.03 |
| 112FA02411 (Non GMP) | 11.31 | 5.68 | 10.41 | 10.23 |
| 112FA02411 (GMP) | 10.58 | 5.79 | 10.16 | 10.25 |

RP-HPLC Confirmation Studies

Figure 5:
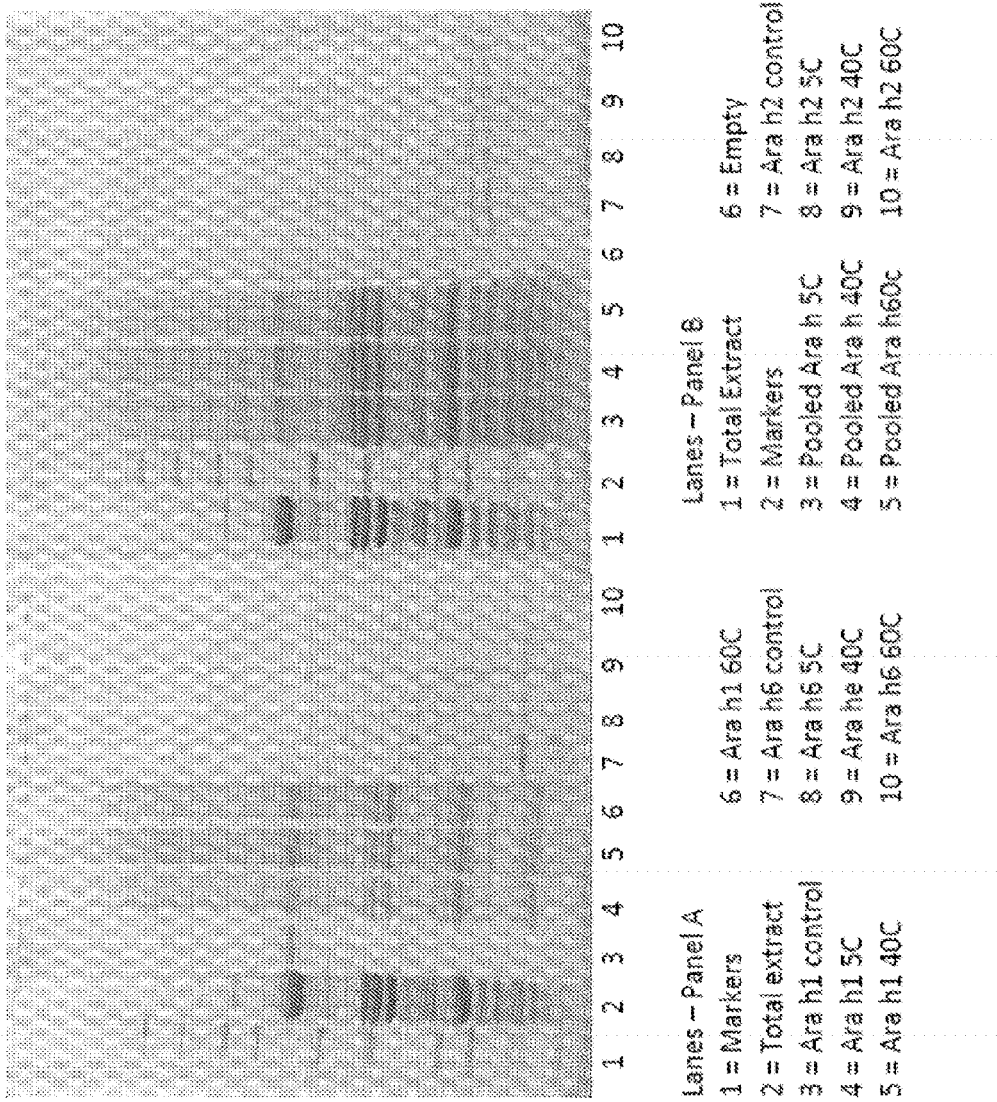
FIG. 5: Total Protein Staining of Pooled and RP-HPLC Purified Ara h Proteins.
Figure 6:
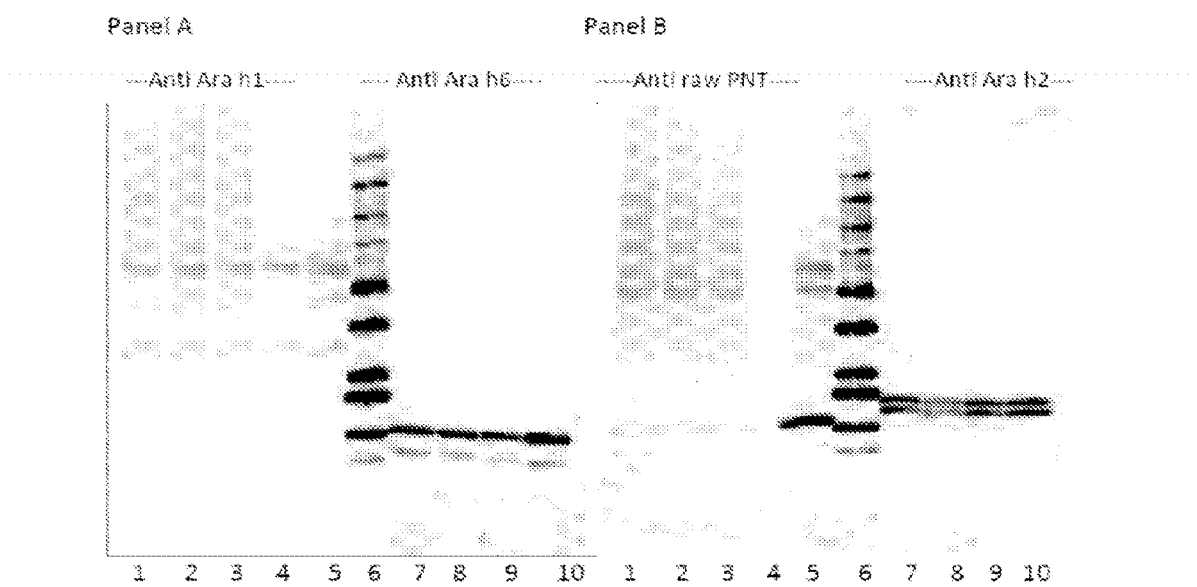
FIG. 6: Immunoblots of Pooled and RP-HPLC Purified Ara h Proteins.

To confirm that the RP-HPLC peak profile actually separates and identifies Ara h1, Ara h2 and Ara h6, material isolated from each peak may be further characterized by SDS polyacrylamide gel electrophoresis using, for example, a 4-20 Novex Tris-HCl pre-cast gel (see, e.g., FIG. 5). Additional gels may be transferred to polyvinylidene difluoride (PVDF) membranes, processed for immunoblotting and may be reacted with Ara h1, Ara h2 or Ara h6 chicken antisera and developed with horse radish peroxidase conjugated goat anti-chicken IgG using, for example, an assay method described by de Jong et al. (*EMBO J.,* 1988; 7(3): 745-750). It should be noted that while extracts may be derived from roasted peanut flour, the antisera may be generated against Ara h proteins purified from raw peanut extracts. The antisera react with both the control Ara h proteins derived from raw peanuts and from the isolated Ara h proteins obtained from roasted peanut extracts (see, e.g., FIG. 6).

The immunoblots show that the material isolated from each of the three principle HPLC peaks was reactive with the appropriate peanut protein specific antisera, and that the molecular weight of the immunoreactive proteins corresponded to the protein molecular weights as reported in the literature (Koppelman et al. 2010). It was determined that the Ara h proteins extracted from the peanut flour are not sensitive to heating to 60° C. Additional confirmatory experiments may be conducted; these assays may be used to establish the most appropriate stability indicating assay that provides the greatest sensitivity to changes occurring during long-term storage. However, the early immunoblot data described herein indicate that the reported RP-HPLC method will track the individual peanut proteins among peanut flour lots.

Source and Testing of the Peanut Flour

Peanut Flour (PF) for use in a formulation described herein may be sourced from any reliable producer including, but not limited to, the Golden Peanut Company (GPC) which manufactures peanut flour and peanut oil (a byproduct of defatting the roasted peanuts).

A GPC manufacturing facility may be audited by an internationally recognized certification body for food safety programs (e.g., Intertek Labtest (UK) Limited). The audit may focus on compliance with the British Retail Consortium Food Standard (BRC) Global Standards for Food Safety. The BRC Global Standards are a leading global safety and quality certification program, used throughout the world by over 17,000 certificated suppliers in 90 countries through a network of over 80 accredited and BRC recognized Certification Bodies. The BRC Global Standards are widely used by suppliers and global retailers. They facilitate standardization of quality, safety, operational criteria and manufacturers' fulfillment of legal obligations. They also help provide protection to the consumer. There were no major or critical non-conformity findings during the most recent audit.

The PF may be about 12% defatted peanut flour milled from lightly roasted peanuts. The PF may be by the supplier after standard analysis of content and microbiology, and is identified as stable for 9 months under refrigeration.

Incoming Raw Material Release Testing for PF

The PF raw material may be tested for appearance, identify, total protein content and moisture content prior to release for cGMP production (see, e.g., Table 4). The PF may be stored under controlled conditions at 2-8° C.

TABLE 4

Raw Material Testing for PF

| Assay | Method | Acceptance Criteria |
|---|---|---|
| Appearance Powder/Color | Visual | Fine powder Tan color |
| Identity | RP-HPLC | Comparable to Reference Chromatogram |
| Protein Content | Nitrogen Content by AOCS Combustion Method for Determination of Crude Protein (AOCS Official Method Ba 4e-93) | Report Results |
| Moisture | Loss on Drying (LOD) USP <921> | Report Results |

Formulation Excipients

Table 5 provides exemplary excipients that may be used in a formulation described herein. Other excipients that may be used in a formulation described herein are provided elsewhere in the description.

Exemplary intended dosage form include, for example, a Hydroxypropyl Methyl Cellulose (HPMC) based capsule; the strength of the dosage form may be about 0.5 mg, about 1 mg. about 10 mg, about 100 mg, about 475 mg, or about 1000 mg of peanut protein. The peanut protein itself, in some instances, may be a cohesive material without inherent flow properties conducive to conventional pharmaceutical manufacturing processes. Thus, inactive pharmaceutical ingredients (excipients) may be added to the formulation so the peanut flower may be developed into a proper pharmaceutical dosage form with flow characteristics to enhance both manufacturing and also delivery of the dosage form.

Compatibility studies may be conducted to evaluate combinations of peanut flour with exemplary excipient categories (diluent, glidant and lubricant). The excipients may have GRAS recognition or be shown to be safe in pharmaceutical formulations. The diluent provides the opportunity to formulate the low and high doses to contain adequate volume for dispersal from the opened capsule. The glidant and lubricant add flowability to the PF such that the capsule is easily emptied of flour by the subject.

As per Table 5 each of the excipients under consideration are designated as USP, NF or USP-NF.

TABLE 5

Excipients Under Consideration

| Functionality | Excipient | Manufacturer (Trade Name) | Grade | Description |
|---|---|---|---|---|
| Diluents | Lactose Monohydrate | Foremost (Lactose 316/Fast-Flo) | NF | Simple Organic Diluent (Monohydrate) |
| | Lactose Anhydrous | Kerry/Sheffield (Lactose DT) | NF | Simple Organic Diluent (Anhydrous) |
| | Mannitol | Roquette (Pearlitol 300DC) | NF | Simple Organic Diluent |
| | Microcrystalline Cellulose | FMC (Avicel pH102) | NF | Complex Organic Diluent |
| | Partially Pregelatinized Corn Starch | Colorcon (Starch 1500) | USP/NF | Complex Organic Diluent |
| | Silicified Microcrystalline Cellulose | JRS Pharma (PROSOLV HD90) | USP | Complex Organic/Inorganic Co-processed Diluent |
| | Dicalcium Phosphate | Innophos (DiTab) | NF | Inorganic Diluent |
| Glidant | Colloidal Silicon Dioxide | Cabot (Cab-O-Sil M5P) | USP | Glidant/Anticaking Agent |
| | Talc | Ultra Chemicals (Ultra Talc 4000) | USP | Glidant/Anticaking Agent |
| Lubricants | Magnesium Stearate (vegetable source) | Mallinckrodt | USP | Lubricant |
| | Sodium Stearyl Fumarate | JRS Pharma (Pruv) | USP | Lubricant |
| Capsule Shell | White Opaque HPMC Capsule Shell | Capsugel (V-Caps) | n/a | Vegetable Source Capsule Shell |
| Capsule Coloring Agents | Pigment Blends | V54.9041 V18.9221 V41.9071 | TBD | Representative of final capsule shell color |
| | Caramel Color | Sensient | TBD | Colorant for matching placebo blends |

Formulation of the Characterized Peanut Allergen

Peanut flour (containing peanut allergen proteins Ara h1, Ara h2 and Ara h6) may be formulated with a bulking and a flow agent in graduated doses, comprising capsules containing 0.5 mg, 1 mg, 10 mg, 100 mg and 1000 mg each of peanut protein.

Low Dose Capsules (0.5 mg and 1 mg)

FIG. 7 and Table 6 outline the proposed blending process for the low dose capsules, which include the 0.5 mg peanut protein and 1 mg peanut protein capsules.

Provided herein is a method of making a low dose capsule formulation useful in the methods provided here, comprising, (a) mixing peanut flour and diluent in a first blend; (b) adding about 45% of diluent in a second blend; (c) adding remaining diluent and/or lubricant in a third blend; (d) adding a glidant in a final blend; and (e) encapsulating blended powder in a capsule. In one embodiment, the diluent of step (a) comprises starch, lactose or microcrystalline cellulose (Avicel®), or dicalcium phosphate. In another embodiment, the diluent of step (b) and/or (c) comprises starch, lactose or microcrystalline cellulose (Avicel®), or dicalcium phosphate. In another embodiment, the glidant of step (d) glidant of step (d) comprises colloidal silicon dioxide (Cab-O-Sil), talc (e.g., Ultra Talc 4000), or combinations thereof. In another embodiment, the glidant of step (d) comprises Cab-O-Sil. In another embodiment, the lubricant of step (d) comprises magnesium stearate. In another embodiment, the method further comprises sampling the blended mixture one or more times prior to encapsulation. In another embodiment, the dose comprises about 0.5 or about 1.0 mg peanut protein. In one embodiment, the method optionally comprises sampling the blended material of step (d). In one embodiment, step (d) comprises adding a glidant or a lubricant. In another embodiment, step (d) comprises adding a glidant and a lubricant.

TABLE 6

Proposed Operation Steps for Low Dose Capsules (0.5 mg and 1 mg)

| Operation Step | Equipment Type | Details | Comments |
|---|---|---|---|
| 1 | Diffusion Blender | V-Blender | Blender shell size TBD based on batch size Use of intensifier bar dependent on uniformity results from developmental batches |
| 2 | Diffusion Blender | V-Blender | Blender shell size TBD based on batch size |
| 3 | Diffusion Blender | V-Blender | Blender shell size TBD based on batch size |
| 4 | Diffusion Blender | V-Blender | Blender shell size TBD based on batch size |
| 5 | Sample Thief | TBD | Thief length and chamber size appropriate for blender size and analytical sample size requirements |
| 6 | Encapsulator | Dosing Disk/ Auger | Encapsulation method TBD based on fill weight variation assessments in developmental batches |

High Dose Capsules (10 mg, 100 mg and 475 mg)

FIG. 8 and Table 7 outline the proposed blending process for the high dose capsules, which include the 10 mg peanut protein, 100 mg peanut protein and 475 mg peanut protein capsules.

Provided herein is a method of making a high dose capsule formulation useful in the methods provided here, comprising, (a) mixing peanut flour and diluent in a first blend; (b) discharging the blended material; (c) passing the blended material through a mesh screen and blending the screened material in a second blend; (d) adding in a glidant and/or lubricant in a third blend; (e) encapsulating the blended powder. In one embodiment, the method optionally comprises sampling the blended material of step (d) one or more times prior to encapsulation. In yet another embodiment, the diluent of step (a) comprises starch, lactose or microcrystalline cellulose (Avicel®), or dicalcium phosphate. In another embodiment, the mesh screen of step (c) comprises a #20 mesh screen. In another embodiment, the glidant of step (d) glidant of step (d) comprises colloidal silicon dioxide (Cab-O-Sil), talc (e.g., Ultra Talc 4000), or combinations thereof. In another embodiment, the glidant of step (d) comprises Cab-O-Sil. In another embodiment, the lubricant of step (d) comprises magnesium stearate. In one embodiment, step (d) comprises adding a glidant or a lubricant. In another embodiment, step (d) comprises adding a glidant and a lubricant.

TABLE 7

Proposed Operation Steps for High Dose Capsules (10 mg, 100 mg and 475 mg)

| Operation Step | Equipment Type | Details | Comments |
|---|---|---|---|
| 1 | Diffusion Blender | V-Blender | Blender shell size TBD based on batch size |
| 2 | Sieve | U.S STD #20 (850 μm) | Promote blend uniformity |
| 3 | Diffusion Blender | V-Blender | Blender shell size TBD based on batch size |
| 4 | Diffusion Blender | V-Blender | Blender shell size TBD based on batch size |
| 5 | Sample Thief | TBD | Thief length and chamber size appropriate for blender size and analytical sample size requirements |
| 6 | Encapsulator | Dosing Disk/ Auger | Encapsulation method TBD based on fill weight variation assessments in developmental batches |

Control of the Bulk Substance

Exemplary proposed specifications for formulated Bulk Substance are summarized in Table 8.

TABLE 8

Proposed Specifications for Bulk Substance

| | Attribute | Method | Acceptance Criteria |
|---|---|---|---|
| General | Appearance Powder/Color | Visual | TBD |
| | Moisture | LOD | Report Results |

TABLE 8-continued Proposed Specifications for Bulk Substance

| | Attribute | Method | Acceptance Criteria |
|---|---|---|---|
| Identity | Presence of Ara h1, Ara h2 and Ara h6 proteins | Reverse Phase HPLC | Comparable to Reference Chromatogram Report percent area of Ara h1, Ara h2 and Ara h6 |
| Strength (Assay) | Total Protein Determination | Nitrogen Content by AOCS Combustion Method for Determination of Crude Protein (AOCS Official Method Ba 4e-93) | Low doses (0.5 and 1 mg): Target protein concentration ± 15% High doses (10, 100 and 475 mg): Target protein concentration ± 10% |
| Safety | Bioburden | Microbiological Limits USP <61> Microbial Enumeration USP <62> Specified Microorganisms | Total Aerobic Microbial Count: NMT 1000 CFU/g Total Yeasts & Molds Count: NMT 100 CFU/g E. coli: Absent S. aureus: Absent P. aeruginosa: Absent Salmonella species: Absent |

Bulk Stability Testing

The formulation may be filled into capsules within 24 hours of blending.

Formulation

Overview of Chemistry and Manufacturing Composition

Peanut flour (containing peanut allergen proteins Ara h1, Ara h2 and Ara h6) may be formulated with a bulking and a flow agent in graduated doses, comprising capsules comprising about 0.5 mg, about 1 mg, about 10 mg, about 100 mg, about 475 mg, or about 1000 mg each of peanut protein with one or more diluents, one or more glidants, one or more lubricants. Optionally one or more filling agents may be added. Each capsule may be opened and the content mixed into taste-masking food immediately prior to administration.

Non-animal capsules that meet global Pharmaceutical standards may be used for the formulations described herein. In one non-limiting embodiment, HPMC capsules from Capsugel may be used.

In another non-limiting embodiment, capsules may be color coded to distinguish the different doses Matching color-coded placebo capsules may also be produced.

TABLE 9

Exemplary Dosage Forms

| | Peanut Protein Dose | Capsule Size |
|---|---|---|
| 1 | 0.5 mg | 3 |
| 2 | 1 mg | 3 |
| 3 | 10 mg | 00 |
| 4 | 100 mg | 00 |
| 5 | 475 mg | 000 |

The final excipient composition of the formulation may be determined after completion of the ongoing compatibility study with the different excipients (see Table 5).

Manufacturing Process

Encapsulation method/equipment may be determined based on fill weight variation assessments in developmental batches. In-process controls may include periodic weight checks.

Control of the Formulation

Exemplary release specifications of the formulations are presented in Table 10.

TABLE 10

Proposed Specifications for the Formulation

| | Attribute | Method | Acceptance Criteria |
|---|---|---|---|
| General | Appearance Powder/color | Visual | TBD |
| | Capsule Integrity | Visual | Intact capsules with no visible signs of cracking. Capsules open easily without breaking |
| | Content Uniformity | USP <905> | Meets USP <905> requirements |
| | Deliverable Mass | % Weight Delivered | Report results |
| | Moisture | Loss on Drying (LOD) USP <921> | Report Results |
| Identity | Presence of Ara h1, Ara h2 and Ara h6 proteins | Reverse Phase HPLC | Comparable to reference chromatogram and Report percent area of Ara h1, Ara h2 and Ara h6 |

TABLE 10-continued

Proposed Specifications for the Formulation

| | Attribute | Method | Acceptance Criteria |
|---|---|---|---|
| Strength (Assay) | Protein Content | Nitrogen Content by AOCS Combustion Method for Determination of Crude Protein (AOCS Official Method Ba 4e-93) | Low doses (0.5 and 1 mg): Target protein concentration ± 15% High doses (10 and 100 mg): Target protein concentration ± 10% |
| Safety | Bioburden | Microbiological Limits USP <61> Microbial Enumeration USP <62> Specified Microorganisms | Total Aerobic Microbial Count: NMT 1000 CFU/g Total Yeasts & Molds Count: NMT 100 CFU/g *E. coli*: Absent *S. aureus*: Absent *P. aeruginosa*: Absent *Salmonella* species: Absent |

Appearance

Appearance assessments may be performed on the bulk substance (e.g., formulation during one or more preparation steps and/or of the final mixture prior to encapsulation) and the formulation. Assessment of the appearance may include, for example, consists of visually inspecting the container against a white background illuminated by a full spectrum light.

Content Uniformity

Content uniformity (CU) of capsules may be performed according to USP standards. Content uniformity may be based on a total protein nitrogen content combustion assay. The intent is to identify a combustion instrument with the sensitivity to enable assaying individual capsules at all doses.

Deliverable Mass

The capsule deliverable mass may be evaluated by weighing capsules, and emptying the contents, and weighing the emptied capsules. The % delivered amount may then be calculated.

Moisture Content

Moisture content may impact the stability of proteins, and understanding the changes in moisture content over time is useful for understanding changes in the formulation that may, in some instances, lead to shorter shelf life. For peanut flour filled capsules, moisture content may be measured using Loss on Drying (LOD) determinations according to the USP. Conditions for the LOD may be determined based on the excipients requirements and requirements for the peanut flour.

Identity (RP-HPLC)

RP-HPLC may be used to confirm identity of the PF, BS and final formulation. Samples may be analyzed according to the methods described in more detail in the related application entitled "Peanut Formulations and Uses Thereof", filed the same day herewith application Ser. No. 61/784,863, which is incorporated herein by reference in its entirety, and the resulting chromatograms may be compared to the example chromatogram provided in the test method (See, e.g., FIG. 9).

A positive identification of peanut flour may be confirmed if the sample chromatogram matches the chromatogram provided in the method. If a positive indication is not confirmed, a lot of peanut flour may be discarded as substandard. Absence of active in placebos may be confirmed by demonstrating that no peaks elute between 12 and 35 minutes in the chromatography.

Total Extractable Protein

A similar approach to the determination of total extractable protein in peanut flour may be used for the determination of total extractable protein in the capsule formulations. The approach may be evaluated for all strengths. In brief, capsule contents may be emptied, weighed, and analyzed by RP-HPLC. Chromatographic analysis of peanut flour samples extracted using this procedure produce a chromatographic "fingerprint" that is unique to peanut flour extracts. The region of the samples that elute between approximately 12 minutes and 35 minutes may be integrated. The total area integrated may be quantitated against a BSA standard. The total extractable protein content may then calculated using the following equation.

$$\text{Mg/g protein} = \frac{R_u}{R_s} \times C_{STD} \times \frac{V_{Sample}}{Wt_{Sample}}$$

where:

$R_u$=Total Ara h Protein Peak Area or Ara h Species Peak Area in the Working Sample;

$R_s$=Average BSA Peak Area in all Working Standards CSTD=BSA Working Standard Concentration (mg/mL);

$V_{sample}$=Total Diluent Volume of the Working Sample (10.0 mL); and $Wt_{sample}$=Weight of peanut flour sample (g).

Apparent Ara h1, Ara h2 and Ara h6 Protein Ratios

Chromatographic analysis of samples extracted using the RP-HPLC method may produce a chromatographic "fingerprint" that is unique to peanut flour extracts, and relative ratios of regions corresponding to Ara h1, Ara h2, and Ara h6 (see, e.g., FIG. 1). The protein content of each of these regions (mg/g) may be quantitated according to the equation provided above. Relative percent content of total protein for each region is then calculated according to the equation below.

$$\text{Ara } h \% = \frac{\text{Ara } h \text{ PeakArea}}{\text{Total/protein PeakArea}} \times 100$$

Protein Content

Protein content in filled capsules may be determined in the same manner as that of the peanut flour (AOCS Official Method Ba 4e-93). Since the accurate protein content determinations may be dependent on the nitrogen content of the sample, no excipients containing nitrogen may be used in the formulation. The method is based on the Dumas method and is based on the combustion of the crude protein in pure oxygen, and measurement of the nitrogen gas that is evolved. The method that may be used may be AOCS Official Method Ba 4e-93. The AOCS Method Definition and Scope are provided below.

Briefly, this method describes a generic combustion method for the determination of crude protein. Combustion at high temperature in pure oxygen frees nitrogen, which is measured by thermal conductivity detection and then converted to equivalent protein by an appropriate numerical factor. This is an alternative method to the mercury catalyst Kjeldahl method and has two advantages: 1) less time is needed for nitrogen determination, and 2) hazardous and toxic chemicals are not utilized.

Stability Testing

Formulations may be stored at 2-8° C. To assess accelerated and long-term stability, formulations may be tested according to the frequency and specifications described in Table 11 and Table 12. Testing for appearance/color, moisture, identity and strength may be performed at all timepoints, and the bioburden may be performed annually at 12, 24, and 36 months.

TABLE 11A

Stability Protocol Testing Scheme for a Formulation

| Temperature | 5° C. +/− 3° C. | 25° C. +/− 2° C. 60% RH |
|---|---|---|
| Testing Frequency | 1, 3, 6, 9, 12, 18, 24, 36 months | 1, 3, 6, 9, 12, 18, 24, 36 months |

Tables 11B-11F provide data obtained by testing stability of various formulations at 5° C.

TABLE 11B

Stability Condition: 5° C. Characterized Peanut Allergen, 475 mg Capsule

| | Specifications | | Stability Intervals | | | |
|---|---|---|---|---|---|---|
| Test | Method | Acceptance Criteria | Initial | 1 Month | 3 Month | 6 Month |
| Identification (HPLC) | TM-074 | Report Area % Ara h1 | 10.18 | 8.5 | 9.67 | 9.31 |
| | | Report Area % Ara h2 | 9.48 | 9.89 | 10.88 | 8.93 |
| | | Report Area % Ara h6 | 5.89 | 5.16 | 5.32 | 4.21 |
| | | Report the ratio of Ara h2/h6 | 1.61 | 1.92 | 2.05 | 2.12 |

TABLE 11C

Stability Condition: 5° C. Characterized Peanut Allergen, 100 mg Capsule

| | Specifications | | Stability Intervals | | | |
|---|---|---|---|---|---|---|
| Test | Method | Acceptance Criteria | Initial | 1 Month | 3 Month | 6 Month |
| Identification (HPLC) | TM-074 | Report Area % Ara h1 | 7.97 | 10.33 | 10.51 | 9.64 |
| | | Report Area % Ara h2 | 8.81 | 8.78 | 9.01 | 8 |
| | | Report Area % Ara h6 | 4.17 | 3.92 | 4.27 | 3.61 |
| | | Report the ratio of Ara h2/h6 | 2.11 | 2.24 | 2.11 | 2.22 |

TABLE 11D

Stability Condition: 5° C. Characterized Peanut Allergen, 10 mg Capsule

| | Specifications | | Stability Intervals | | | |
|---|---|---|---|---|---|---|
| Test | Method | Acceptance Criteria | Initial | 1 Month | 3 Month | 6 Month |
| Identification (HPLC) | TM-074 | Report Area % Ara h1 | 6.66 | 7.71 | 9.36 | 7.11 |
| | | Report Area % Ara h2 | 10.95 | 9.75 | 9.54 | 10.16 |
| | | Report Area % Ara h6 | 5.93 | 5.8 | 5.55 | 5.51 |
| | | Report the ratio of Ara h2/h6 | 1.85 | 1.68 | 1.72 | 1.84 |

TABLE 11E

Stability Condition: 5° C. Characterized Peanut Allergen, 1.0 mg Capsule

| | Specifications | | Stability Intervals | | | |
|---|---|---|---|---|---|---|
| Test | Method | Acceptance Criteria | Initial | 1 Month | 3 Month | 6 Month |
| Identification (HPLC) | TM-074 | Report Area % Ara h1 | 7.35 | 7.43 | 8.54 | 7.65 |
| | | Report Area % Ara h2 | 16.11 | 14.39 | 12.31 | 12.94 |
| | | Report Area % Ara h6 | 7.14 | 6.56 | 5.77 | 6.36 |
| | | Report the ratio of Ara h2/h6 | 2.26 | 2.19 | 2.13 | 2.03 |

TABLE 11F

Stability Condition: 5° C. Characterized Peanut Allergen, 0.5 mg Capsule

| Test | Method | Acceptance Criteria | Initial | 1 Month | 3 Month | 6 Month | 9 Month |
|---|---|---|---|---|---|---|---|
| Identification (HPLC) | TM-074 | Report Area % Ara h1 | 7.12 | 8.25 | 8.3 | 8 | 6.09 |
| | | Report Area % Ara h2 | 19.37 | 14.76 | 15.26 | 16.15 | 20.78 |
| | | Report Area % Ara h6 | 8.77 | 8.69 | 8.9 | 8.8 | 10.38 |
| | | Report the ratio of Ara h2/h6 | 2.21 | 1.7 | 1.71 | 1.84 | 2.00 |

Tables 11G-11K provide data obtained by testing stability of various formulations at 25° C.

TABLE 11G

Stability Condition: 25° C. Characterized Peanut Allergen, 475 mg Capsule

| Test | Method | Acceptance Criteria | Initial | 1 Month | 3 Month | 6 Month |
|---|---|---|---|---|---|---|
| Identification (HPLC) | TM-074 | Report Area % Ara h1 | 10.18 | 8.26 | 10.1 | 9.93 |
| | | Report Area % Ara h2 | 9.48 | 9.86 | 10.48 | 9.77 |
| | | Report Area % Ara h6 | 5.89 | 5.09 | 5.25 | 4.41 |
| | | Report the ratio of Ara h2/h6 | 1.61 | 1.94 | 2 | 2.22 |

TABLE 11H

Stability Condition: 25° C. Characterized Peanut Allergen, 100 mg Capsule

| Test | Method | Acceptance Criteria | Initial | 1 Month | 3 Month | 6 Month |
|---|---|---|---|---|---|---|
| Identification (HPLC) | TM-074 | Report Area % Ara h1 | 7.97 | 9.92 | 10.42 | 9.75 |
| | | Report Area % Ara h2 | 8.81 | 8.32 | 9.4 | 8.04 |
| | | Report Area % Ara h6 | 4.17 | 4.18 | 4.28 | 3.6 |
| | | Report the ratio of Ara h2/h6 | 2.11 | 1.99 | 2.2 | 2.23 |

TABLE 11I

Stability Condition: 25° C. Characterized Peanut Allergen, 10 mg Capsule

| Test | Method | Acceptance Criteria | Initial | 1 Month | 3 Month | 6 Month |
|---|---|---|---|---|---|---|
| Identification (HPLC) | TM-074 | Report Area % Ara h1 | 6.66 | 7.99 | 9.47 | 7.26 |
| | | Report Area % Ara h2 | 10.95 | 10.77 | 10.23 | 10.11 |
| | | Report Area % Ara h6 | 5.93 | 5.81 | 4.99 | 5.83 |
| | | Report the ratio of Ara h2/h6 | 1.85 | 1.85 | 2.05 | 1.73 |

TABLE 11J

Stability Condition: 25° C. Characterized Peanut Allergen, 1.0 mg Capsule

| Test | Method | Acceptance Criteria | Initial | 1 Month | 3 Month | 6 Month |
|---|---|---|---|---|---|---|
| Identification (HPLC) | TM-074 | Report Area % Ara h1 | 7.35 | 7.63 | 8.24 | 7.74 |
| | | Report Area % Ara h2 | 16.11 | 12.59 | 12.97 | 12.89 |
| | | Report Area % Ara h6 | 7.14 | 6.55 | 5.81 | 6.05 |
| | | Report the ratio of Ara h2/h6 | 2.26 | 1.92 | 2.23 | 2.13 |

TABLE 11K

Stability Condition: 25° C. Characterized Peanut Allergen, 0.5 mg Capsule

| Test | Method | Acceptance Criteria | Initial | 1 Month | 3 Month | 6 Month | 9 Month |
|---|---|---|---|---|---|---|---|
| Identification (HPLC) | TM-074 | Report Area % Ara h1 | 7.12 | 8.22 | 7.95 | 7.83 | 6.16 |

TABLE 11K-continued

Stability Condition: 25° C. Characterized Peanut Allergen, 0.5 mg Capsule

| Test | Method | Acceptance Criteria | Initial | 1 Month | 3 Month | 6 Month | 9 Month |
|---|---|---|---|---|---|---|---|
| | | Report Area % Ara h2 | 19.37 | 9.49 | 16.3 | 16.28 | 20.92 |
| | | Report Area % Ara h6 | 8.77 | 15 | 8.76 | 8.2 | 9.47 |
| | | Report the ratio of Ara h2/h6 | 2.21 | 1.58 | 1.86 | 1.99 | 2.21 |

TABLE 12A

Stability Protocol Specifications for a Formulation

| | Attribute | Method | Acceptance Criteria |
|---|---|---|---|
| General | Appearance Powder/color | Visual | TBD |
| | Capsule Integrity | Visual | Intact capsules with no visible signs of cracking. Capsules open easily without breaking |
| | Moisture | Loss on Drying (LOD) USP <921> | Report Results |
| Identity | Presence of Ara h1, Ara h2 and Ara h6 proteins | Reverse Phase HPLC | Comparable to reference chromatogram and report percent area of Ara h1, Ara h2 and Ara h6 |
| Strength (Assay) | Protein Content | Nitrogen Content by AOCS Combustion Method for Determination of Crude Protein (AOCS Official Method Ba 4e-93) | Low doses (0.5 and 1 mg): Target protein concentration ± 15% High doses (10 and 100 mg): Target protein concentration ± 10% |
| Safety | Bioburden* | Microbiological Limits USP <61> Microbial Enumeration USP <62> Specified Microorganisms | Total Aerobic Microbial Count: NMT 1000 CFU/g Total Yeasts & Molds Count: NMT 100 CFU/g E. coli: Absent S. aureus: Absent P. aeruginosa: Absent Salmonella species: Absent |

*Bioburden may be measured at release and annually.

Tables 12B-12K provide data obtained by assessing stability and characteristics of various formulations at 5° C. and 25° C. at various time points.

TABLE 12B

Stability Conditions: 5° C.; 0.5 mg capsule

| Test | Method | Acceptance Criteria | Initial | 1 Mo | 3 Mo | 6 Mo | 9 Mo |
|---|---|---|---|---|---|---|---|
| Appearance (n = 10) | Visual | White opaque capsule containing white to off-white fine granular powder* | Conforms | Conforms | Conforms | Conforms | Conforms |

TABLE 12B-continued

Stability Conditions: 5° C.; 0.5 mg capsule

| | Specifications | | | | Stability Intervals | | |
|---|---|---|---|---|---|---|---|
| Test | Method | Acceptance Criteria | Initial | 1 Mo | 3 Mo | 6 Mo | 9 Mo |
| Deliverable Mass | TM-086 | >95%* | Average: 99%; RSD: 0.4% | Average: 99%; RSD: 0.5% | Average: 100%; RSD: 0.3% | Average: 99%; RSD: 0.1% | Average: 99%; RSD: 0.6% |
| Assay | TM-085 | Target protein concentration ± 15% | 91% | 88% | 92% | 101% | 88% |
| Identification (HPLC) | TM-074 | Comparable to reference chromatogram | Comparable | Comparable | Comparable | Comparable | Comparable |
| | | Report Area % Ara h1 | 7.12 | 8.25 | 8.3 | 8 | 6.09 |
| | | Report Area % Ara h2 | 19.37 | 14.76 | 15.26 | 16.15 | 20.78 |
| | | Report Area % Ara h6 | 8.77 | 8.69 | 8.9 | 8.8 | 10.38 |
| | | Report the ratio of Ara h2/h6 | 2.21 | 1.7 | 1.71 | 1.84 | 2.00 |
| Loss on Drying (@130° C. for 2 hours) | USP <731> | Report Results | 3.83% | 4.00% | 4.50% | 6.40% | 5.40% |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA | NA |

TABLE 12C

Stability Condition: 25° C./60% RH; 0.5 mg capsule

| | Specifications | | | | Stability Intervals | | |
|---|---|---|---|---|---|---|---|
| Test | Method | Acceptance Criteria | Initial | 1 Mo | 3 Mo | 6 Mo | 9 Mo |
| Appearance (n = 10) | Visual | White opaque capsule containing white to off-white fine granular powder* | Conforms | Conforms | Conforms | Conforms | Conforms |
| Deliverable Mass | TM-086 | >95%* | Average: 99% RSD: 0.4% | Average: 100% RSD: 0.5% | Average: 99% RSD: 0.4% | Average: 100% RSD: 0.3% | Average: 99% RSD: 0.7% |
| Assay | TM-085 | Target protein concentration ± 15%; (85-115% label claim) | 91% | 90% | 90% | 98% | 82% |
| Identification (HPLC) | TM-074 | Comparable to reference chromatogram | Comparable | Comparable | Comparable | Comparable | Comparable |
| | | Report Area % Ara h1 | 7.12 | 8.22 | 7.95 | 7.83 | 6.16 |
| | | Report Area % Ara h2 | 19.37 | 9.49 | 16.3 | 16.28 | 20.92 |
| | | Report Area % Ara h6 | 8.77 | 15 | 8.76 | 8.2 | 9.47 |
| | | Report the ratio of Ara h2/h6 | 2.21 | 1.58 | 1.86 | 1.99 | 2.21 |

TABLE 12C-continued

Stability Condition: 25° C./60% RH; 0.5 mg capsule

| Test | Specifications | | Stability Intervals | | | | |
|---|---|---|---|---|---|---|---|
| | Method | Acceptance Criteria | Initial | 1 Mo | 3 Mo | 6 Mo | 9 Mo |
| Loss on Drying (@130° C. for 2 hours) | USP <731> | Report Results | 3.83% | 3.70% | 4.20% | 4.10% | 4.60% |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA | NA |

TABLE 12D

Stability Condition: 5° C.: Characterized Peanut Allergen, 1.0 mg Capsule

| Test | Specifications | | Stability Intervals | | | |
|---|---|---|---|---|---|---|
| | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.3% | Average: 100%; RSD: 0.4% | Average: 99%; RSD: 0.6% | Average: 99%; RSD: 0.3% |
| Assay | TM-085 | Target protein concentration ± 15%; (85-115% label claim) | 101% | 90% | 86% | 94% |
| Identification (HPLC) | TM-074 | Comparable to reference chromatogram | Comparable | Comparable | Comparable | Comparable |
| | | Report Area % Ara h1 | 7.35 | 7.43 | 8.54 | 7.65 |
| | | Report Area % Ara h2 | 16.11 | 14.39 | 12.31 | 12.94 |
| | | Report Area % Ara h6 | 7.14 | 6.56 | 5.77 | 6.36 |
| | | Report the ratio of Ara h2/h6 | 2.26 | 2.19 | 2.13 | 2.03 |
| Loss on Drying (@130° C. for 2 hours) | USP <731> | Report Results | 5.02% | 5.20% | 5.70% | 6.20% |

TABLE 12D-continued

Stability Condition: 5° C.: Characterized Peanut Allergen, 1.0 mg Capsule

| Test | Specifications | | Stability Intervals | | | |
|---|---|---|---|---|---|---|
| | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12E

Stability Condition: 25° C./60% RH; Characterized Peanut Allergen, 1.0 mg Capsule

| Test | Specifications | | Stability Intervals | | | |
|---|---|---|---|---|---|---|
| | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.3% | Average: 100%; RSD: 0.3% | Average: 99%; RSD: 0.2% | Average: 100%; RSD: 0.3% |
| Assay | TM-085 | Target protein concentration ± 15%; (85-115% label claim) | 101% | 90% | 87% | 94% |
| Identification (HPLC) | TM-074 | Comparable to reference chromatogram | Comparable | Comparable | Comparable | Comparable |
| | | Report Area % Ara h1 | 7.35 | 7.63 | 8.24 | 7.74 |
| | | Report Area % Ara h2 | 16.11 | 12.59 | 12.97 | 12.89 |
| | | Report Area % Ara h6 | 7.14 | 6.55 | 5.81 | 6.05 |
| | | Report the ratio of Ara h2/h6 | 2.26 | 1.92 | 2.23 | 2.13 |
| Loss on Drying (@130° C. for 2 hours) | USP <731> | Report Results | 5.02% | 5.00% | 5.80% | 6.10% |

TABLE 12E-continued

Stability Condition: 25° C./60% RH; Characterized Peanut Allergen, 1.0 mg Capsule

| Test | Specifications Method | Acceptance Criteria | Stability Intervals Initial | 1 Mo | 3 Mo | 6 Mo |
|---|---|---|---|---|---|---|
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12F

Stability Condition: 5° C.; Characterized Peanut Allergen, 10 mg Capsule

| Test | Specifications Method | Acceptance Criteria | Stability Intervals Initial | 1 Mo | 3 Mo | 6 Mo |
|---|---|---|---|---|---|---|
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.2% | Average: 100%; RSD: 0.1% | Average: 100%; RSD: 0.1% | Average: 100%; RSD: 0.1% |
| Assay | TM-085 | Target protein concentration ± 10% (90-110% label claim) | 95% | 93% | 96% | 98% |
| Identification (HPLC) | TM-074 | Comparable to reference chromatogram | Comparable | Comparable | Comparable | Comparable |
| | | Report Area % Ara h1 | 6.66 | 7.71 | 9.36 | 7.11 |
| | | Report Area % Ara h2 | 10.95 | 9.75 | 9.54 | 10.16 |
| | | Report Area % Ara h6 | 5.93 | 5.8 | 5.55 | 5.51 |
| | | Report the ratio of Ara h2/h6 | 1.85 | 1.68 | 1.72 | 1.84 |
| Loss on Drying (@130° C. for 2 hours) | USP <731> | Report Results | 4.90% | 5.60% | 5.40% | 5.50% |

TABLE 12F-continued

Stability Condition: 5° C.; Characterized Peanut Allergen, 10 mg Capsule

| Test | Specifications | | Stability Intervals | | | |
|---|---|---|---|---|---|---|
| | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12G

Stability Condition: 25° C./60% RH; Characterized Peanut Allergen, 10 mg Capsule

| Test | Specifications | | Stability Intervals | | | |
|---|---|---|---|---|---|---|
| | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.2% | Average: 100%; RSD: 0.2% | Average: 100%; RSD: 0.1% | Average: 100%; RSD: 0.1% |
| Assay | TM-085 | Target protein concentration ± 10% (90-110% label claim) | 95% | 93% | 93% | 97% |
| Identification (HPLC) | TM-074 | Comparable to reference chromatogram | Comparable | Comparable | Comparable | Comparable |
| | | Report Area % Ara h1 | 6.66 | 7.99 | 9.47 | 7.26 |
| | | Report Area % Ara h2 | 10.95 | 10.77 | 10.23 | 10.11 |
| | | Report Area % Ara h6 | 5.93 | 5.81 | 4.99 | 5.83 |
| | | Report the ratio of Ara h2/h6 | 1.85 | 1.85 | 2.05 | 1.73 |
| Loss on Drying (@130° C. for 2 hours) | USP <731> | Report Results | 4.90% | 4.60% | 5.20% | 5.20% |

TABLE 12G-continued

Stability Condition: 25° C./60% RH; Characterized Peanut Allergen, 10 mg Capsule

| | Specifications | | Stability Intervals | | | |
|---|---|---|---|---|---|---|
| Test | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12H

Stability Condition: 5° C.; Characterized Peanut Allergen, 100 mg Capsule

| | Specifications | | Stability Intervals | | | |
|---|---|---|---|---|---|---|
| Test | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.1% | Average: 100%; RSD: 0.2% | Average: 100%; RSD: 0.1% | Average: 100%; RSD: 0.1% |
| Assay | TM-085 | Target protein concentration ± 10% (90-110% label claim) | 99% | 95% | 99% | 99% |
| Identification (HPLC) | TM-074 | Comparable to reference chromatogram | Comparable | Comparable | Comparable | Comparable |
| | | Report Area % Ara h1 | 7.97 | 10.33 | 10.51 | 9.64 |
| | | Report Area % Ara h2 | 8.81 | 8.78 | 9.01 | 8 |
| | | Report Area % Ara h6 | 4.17 | 3.92 | 4.27 | 3.61 |
| | | Report the ratio of Ara h2/h6 | 2.11 | 2.24 | 2.11 | 2.22 |
| Loss on Drying (@130° C. for 2 hours) | USP <731> | Report Results | 4.02% | 3.70% | 4.40% | 4.40% |

TABLE 12H-continued

Stability Condition: 5° C.; Characterized Peanut Allergen, 100 mg Capsule

| | Specifications | | Stability Intervals | | | |
|---|---|---|---|---|---|---|
| Test | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12I

Stability Condition: 25° C.; Characterized Peanut Allergen, 100 mg Capsule

| | Specifications | | Stability Intervals | | | |
|---|---|---|---|---|---|---|
| Test | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.1% | Average: 100%; RSD: 0.1% | Average: 100%; RSD: 0.1% | Average: 100%; RSD: 0.4% |
| Assay | TM-085 | Target protein concentration ± 10% (90-110% label claim) | 99% | 96% | 98% | 97% |
| Identification (HPLC) | TM-074 | Comparable to reference chromatogram | Comparable | Comparable | Comparable | Comparable |
| | | Report Area % Ara h1 | 7.97 | 9.92 | 10.42 | 9.75 |
| | | Report Area % Ara h2 | 8.81 | 8.32 | 9.4 | 8.04 |
| | | Report Area % Ara h6 | 4.17 | 4.18 | 4.28 | 3.6 |
| | | Report the ratio of Ara h2/h6 | 2.11 | 1.99 | 2.2 | 2.23 |
| Loss on Drying (@130° C. for 2 hours) | USP <731> | Report Results | 4.02% | 4.00% | 4.40% | 4.80% |

TABLE 12I-continued

Stability Condition: 25° C.; Characterized Peanut Allergen, 100 mg Capsule

| Test | Specifications | | Stability Intervals | | | |
|---|---|---|---|---|---|---|
| | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12J

Stability Condition: 5° C.; Characterized Peanut Allergen, 475 mg Capsule

| Test | Specifications | | Stability Intervals | | | |
|---|---|---|---|---|---|---|
| | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.0% | Average: 100%; RSD: 0.1% | Average: 100%; RSD: 0.0% | Average: 100%; RSD: 0.1% |
| Assay | TM-085 | Target protein concentration ± 10% (90-110% label claim) | 90% | 94% | 96% | 96% |
| Identification (HPLC) | TM-074 | Comparable to reference chromatogram | Comparable | Comparable | Comparable | Comparable |
| | | Report Area % Ara h1 | 10.18 | 8.5 | 9.67 | 9.31 |
| | | Report Area % Ara h2 | 9.48 | 9.89 | 10.88 | 8.93 |
| | | Report Area % Ara h6 | 5.89 | 5.16 | 5.32 | 4.21 |
| | | Report the ratio of Ara h2/h6 | 1.61 | 1.92 | 2.05 | 2.12 |
| Loss on Drying (@130° C. for 2 hours) | USP <731> | Report Results | 4.00% | 3.60% | 3.70% | 3.90% |

TABLE 12J-continued

Stability Condition: 5° C.; Characterized Peanut Allergen, 475 mg Capsule

| Test | Specifications | | Stability Intervals | | | |
|---|---|---|---|---|---|---|
| | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

TABLE 12K

Stability Condition: 25° C.; Characterized Peanut Allergen, 475 mg Capsule

| Test | Specifications | | Stability Intervals | | | |
|---|---|---|---|---|---|---|
| | Method | Acceptance Criteria | Initial | 1 Mo | 3 Mo | 6 Mo |
| Appearance (n = 10) | Visual | White opaque capsule containing white to off-white fine granular powder* | Conforms | Conforms | Conforms | Conforms |
| Deliverable Mass | TM-086 | >95%* | Average: 100%; RSD: 0.0% | Average: 100%; RSD: 0.1% | Average: 100%; RSD: 0.1% | Average: 100%; RSD: 0.1% |
| Assay | TM-085 | Target protein concentration ± 10% (90-110% label claim) | 90% | 95% | 96% | 95% |
| Identification (HPLC) | TM-074 | Comparable to reference chromatogram | Comparable | Comparable | Comparable | Comparable |
| | | Report Area % Ara h1 | 10.18 | 8.26 | 10.1 | 9.93 |
| | | Report Area % Ara h2 | 9.48 | 9.86 | 10.48 | 9.77 |
| | | Report Area % Ara h6 | 5.89 | 5.09 | 5.25 | 4.41 |
| | | Report the ratio of Ara h2/h6 | 1.61 | 1.94 | 2 | 2.22 |
| Loss on Drying (@130° C. for 2 hours) | USP <731> | Report Results | 4.00% | 3.80% | 4.10% | 4.50% |

TABLE 12K-continued

Stability Condition: 25° C.; Characterized Peanut Allergen, 475 mg Capsule

| Test | Specifications | | Stability Intervals | | | |
|---|---|---|---|---|---|---|
| | Method | Acceptance Criteria | Initial | 1 Mo | 3 Mo | 6 Mo |
| Microbial Limits/ Specified Microorganisms | USP <61> and <62> Quality Chemical Laboratories | Total Aerobic Microbial Count: NMT 1000 cfu/g; Total Combined Yeasts & Molds Count: NMT 100 cfu/g; *E. coli*, *S. aureus*, *P. aeruginosa* and *Salmonella* species are absent | Meets Acceptance Criteria | NA | NA | NA |

Placebo

Placebo may consist of the defined mixture of excipients without the PF. Placebo may be filled in the same color-coded capsules as the active formulation.

TABLE 13

Placebo Release Specification

| | Attribute | Method | Acceptance Criteria |
|---|---|---|---|
| General | Appearance Powder/color | Visual | TBD |
| | Capsule Integrity | Visual | Intact capsules with no visible signs of cracking. Capsules open easily without breaking |
| | Content Uniformity | USP <905> | Meets USP <905> requirements |
| | Deliverable Mass | % Weight Delivered | Report results |
| | Moisture | Loss on Drying (LOD) USP <921> | Report Results |
| Identity | Absence of Ara h1, Ara h2 and Ara h6 proteins | Reverse Phase HPLC | No peaks detected in the elution region of PF |
| Strength (Assay) | Protein Content | Nitrogen Content by AOCS Combustion Method for Determination of Crude Protein (AOCS Official Method Ba 4e-93) | No protein detected |
| Safety | Bioburden | Microbiological Limits USP <61> Microbial Enumeration USP <62> Specified Microorganisms | Total Aerobic Microbial Count: NMT 1000 CFU/g Total Yeasts & Molds Count: NMT 100 CFU/g *E. coli*: Absent *S. aureus*: Absent *P. aeruginosa*: Absent *Salmonella* species: Absent |

Methods of Use

The pharmaceutical compositions prepared using the methods described herein may be used to compare various lots of peanut proteins for consistency of product.

Peanuts and peanut flour are common foods and additives found in many food products. The intended clinical use for Characterized Peanut Allergen (CPA) is found in relatively small quantities (0.5 to 4000 mg/dose) compared to quantities contained in food and will be delivered via the same route as orally ingested peanut-containing products.

Currently, preclinical studies exploring treatment modalities in food allergy animal models are limited. The principle model for induction of peanut allergy in mice is to expose mice by oral gavage to peanut proteins in the form of peanut butter, ground roasted peanuts, or purified peanut proteins, in combination with cholera toxin. After 3 to 6 weekly exposures the mice are challenged to demonstrate an allergic response. Mice may be challenged by intraperitoneal injection with sub-lethal doses of with a formulation described herein and scored for reaction severity. The intent is to demonstrate that the principle elicitors of anaphylaxis are specific Ara h proteins, rather than a combination of all peanut proteins. In an immunotherapy protocol, mice are treated with whole peanut extract, extract depleted of Ara h proteins, or with purified Ara h proteins alone. Upon challenge post treatment, changes in body temperature, symptom score and mouse mast cell protease-1 release mice may be assessed. Mice that are desensitized to further challenge may be treated with an entire extract or the Ara h protein combination.

The cellular requirements underlying peanut induced anaphylaxis may be determined explored in wild-type C57BL/6, B-cell deficient, CD40L-deficient, mast cell deficient or FcεRI ε-chain-deficient mice sensitized to peanut proteins. After intraperitoneal challenge with a formulation described herein, anaphylaxis is assessed by measurement of antigen-specific immunoglobulins (Igs), overall symptom score, body temperature, vascular permeability, mast cell mediator release and anaphylactic reactions. The B-cell, mast cell and CD40L deficient mice may be sensitized to peanut proteins as shown by production of IgE, and Th2-associated cytokines. The FcεRI ε-deficient mice may experience anaphylaxis albeit somewhat less severe than the wild-type animals.

In a model of esophago-gastro-enteropathy induced by long term feeding of peanuts to sensitized mice described by Mondoulet et al., 2012, epicutaneous immunotherapy with a formulation described herein may lessen the severity of gastro-intestinal lesions. (Mondoulet et al., 2012).

Data obtained from these models, which may demonstrate one or more of the hallmarks of human food allergic reactions, and are to be considered with respect to variability of human food allergy.

Provided herein is a method of identifying a composition for treatment for desensitization of peanut allergy in a subject, comprising: (a) determining the concentrations of Ara h1, Ara h2 and Ara h6 in a composition of peanut flour by RP-HPLC; (b) comparing the concentrations to the concentrations of a reference standard; and (c) identifying a composition for desensitization of peanut allergy in a subject, wherein the sample contains at least the concentrations of Ara h1, Ara h2 and Ara h6 of the reference standard.

The method may, in some instances, further comprise administering a composition described herein to a subject, wherein the composition comprises at least the concentrations of Ara h1, Ara h2 and Ara h6 of the reference standard.

The method may be used to compare lots of peanut flour and, in some instances, exclude peanut flour from use in a composition or method described herein where the sample does not contain at least the reference standard amount of Ara h1, Ara h2 and Ara h6.

While preferred embodiments have been shown and described herein, it will be obvious to those skilled in the art that such embodiments are provided by way of example only. Numerous variations, changes, and substitutions may now occur to those skilled in the art without departing from the embodiments. It should be understood that various alternatives to the embodiments described herein may be employed in practicing the embodiments. It is intended that the following claims define the scope of the embodiments and that methods and structures within the scope of these claims and their equivalents be covered thereby.

What is claimed is:

1. A method of making an allergenic peanut flour formulation, comprising:
   (a) providing defatted peanut flour;
   (b) characterizing a concentration of each of Ara h1, Ara h2, and Ara h6 in the defatted peanut flour; and
   (c) mixing the defatted peanut flour comprising the characterized concentration of each of Ara h1, Ara h2, and Ara h6 with a lubricant, a glidant, or a diluent to form the allergenic peanut flour formulation.

2. The method of claim 1, wherein characterizing the concentration of each of Ara h1, Ara h2, and Ara h6 in the defatted peanut flour comprises determining a relative concentration of each of Ara h1, Ara h2, and Ara h6 compared to a total peanut protein content in the defatted peanut flour.

3. The method of claim 1, wherein characterizing the concentration of each of Ara h1, Ara h2, and Ara h6 in the defatted peanut flour comprises determining a relative concentration of each of Ara h1, Ara h2, and Ara h6 compared to each other in the defatted peanut flour.

4. The method of claim 1, wherein the concentration of each of Ara h1, Ara h2, and Ara h6 are characterized by Reverse Phased-High Performance Liquid Chromatography (RP-HPLC).

5. The method of claim 1, further comprising monitoring lot-to-lot consistency of Ara h1, Ara h2, and Ara h6.

6. The method of claim 1, further comprising packaging the allergenic peanut flour formulation in a pharmaceutical dosage form.

7. The method of claim 6, wherein the pharmaceutical dosage form comprises about 0.5 mg to about 1000 mg of peanut protein.

8. The method of claim 1, further comprising encapsulating the allergenic peanut flour formulation in a capsule.

9. The method of claim 8, wherein the capsule comprises about 0.5 mg to about 1000 mg of peanut protein.

10. The method of claim 1, wherein the defatted peanut flour is about 10% to about 15% defatted peanut flour.

11. The method of claim 1, wherein the defatted peanut flour is about 12% defatted peanut flour.

12. The method of claim 1, further comprising discharging the allergenic peanut flour formulation.

13. The method of claim 1, further comprising passing the allergenic peanut flour formulation through a mesh screen.

14. A method of making an allergenic peanut flour formulation, comprising:
   (a) mixing a defatted peanut flour with a lubricant, a glidant, or a diluent to form the allergenic peanut flour formulation; and
   (b) characterizing a concentration of each of Ara h1, Ara h2, and Ara h6 in the allergenic peanut flour formulation.

15. The method of claim 14, wherein characterizing the concentration of each of Ara h1, Ara h2, and Ara h6 in the allergenic peanut flour formulation comprises determining a relative concentration of each of Ara h1, Ara h2, and Ara h6 compared to a total peanut protein content in the peanut flour formulation.

16. The method of claim 14, wherein characterizing the concentration of each of Ara h1, Ara h2, and Ara h6 in the allergenic peanut flour formulation comprises determining a relative concentration of each of Ara h1, Ara h2, and Ara h6 compared to each other in the allergenic peanut flour formulation.

17. The method of claim 14, wherein the concentration of each of Ara h1, Ara h2, and Ara h6 are characterized by Reverse Phased-High Performance Liquid Chromatography (RP-HPLC).

18. The method of claim 14, further comprising monitoring lot-to-lot consistency of Ara h1, Ara h2, and Ara h6.

19. The method of claim 14, further comprising packaging the allergenic peanut flour formulation in a pharmaceutical dosage form.

20. The method of claim 19, wherein the pharmaceutical dosage form comprises about 0.5 mg to about 1000 mg of peanut protein.

21. The method of claim 14, further comprising encapsulating the allergenic peanut flour formulation in a capsule.

22. The method of claim 21, wherein the capsule comprises about 0.5 mg to about 1000 mg of peanut protein.

23. The method of claim 14, wherein the defatted peanut flour is about 10% to about 15% defatted peanut flour.

24. The method of claim 14, wherein the defatted peanut flour is about 12% defatted peanut flour.

25. The method of claim 14, further comprising discharging the allergenic peanut flour formulation.

26. The method of claim 14, further comprising passing the allergenic peanut flour formulation through a mesh screen.

* * * * *